(12) United States Patent
Chu

(10) Patent No.: US 9,381,075 B2
(45) Date of Patent: Jul. 5, 2016

(54) DEFLECTION MEMBER FOR DELIVERING IMPLANTS AND METHODS OF DELIVERING IMPLANTS

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 208 days.

(21) Appl. No.: 13/358,270

(22) Filed: Jan. 25, 2012

(65) Prior Publication Data

US 2012/0197281 A1 Aug. 2, 2012

Related U.S. Application Data

(60) Provisional application No. 61/437,877, filed on Jan. 31, 2011.

(51) Int. Cl.
| | | |
|---|---|---|
| *A61F 2/00* | (2006.01) | |
| *A61B 17/04* | (2006.01) | |
| *A61B 17/06* | (2006.01) | |
| *A61B 17/062* | (2006.01) | |
| *A61B 17/00* | (2006.01) | |

(52) U.S. Cl.
CPC ........... *A61F 2/0004* (2013.01); *A61B 17/0482* (2013.01); *A61B 17/062* (2013.01); *A61B 17/06109* (2013.01); *A61B 2017/00805* (2013.01)

(58) Field of Classification Search
CPC ............ A61B 17/0482; A61B 17/062; A61B 17/06109; A61B 2017/00805; A61B 17/3468; A61F 2/0045
USPC ..................... 600/37; 606/151–157
See application file for complete search history.

(56) References Cited

U.S. PATENT DOCUMENTS

| | | | | |
|---|---|---|---|---|
| 2,740,404 | A | * 4/1956 | Kohl | ............... 604/167.01 |
| 4,373,530 | A | 2/1983 | Kilejian | |
| 4,966,143 | A | * 10/1990 | Meinershagen | .............. 606/103 |
| 5,337,736 | A | 8/1994 | Reddy | |
| 5,362,294 | A | 11/1994 | Seitzinger | |

(Continued)

FOREIGN PATENT DOCUMENTS

| | | |
|---|---|---|
| EP | 2001398 B1 | 5/2010 |
| GB | 2353220 A | 2/2001 |
| WO | 02078548 A1 | 10/2002 |
| WO | 2009018372 A3 | 2/2009 |

OTHER PUBLICATIONS

Search Report and Written Opinion for International Application No. PCT/US2012/022944, mailed Jun. 22, 2012, 18 pages.

(Continued)

*Primary Examiner* — Navin Natnithithadha
*Assistant Examiner* — Kaylee Wilson
(74) *Attorney, Agent, or Firm* — Brake Hughes Bellermann LLP

(57) ABSTRACT

In one general aspect, an apparatus can include an elongate member configured to be associated with an implant and having a piercing portion. The apparatus can include a deflection member having a fixed curvature disposed within a plane. The deflection member can have a distal end configured to be disposed within a body of a patient. The deflection member can define a groove extending along at least a portion of the deflection member. The groove of the deflection member can be configured to deflect the piercing portion of the elongate member.

8 Claims, 21 Drawing Sheets

(56) References Cited

U.S. PATENT DOCUMENTS

| | | |
|---|---|---|
| 5,383,904 A | 1/1995 | Totakura et al. |
| 5,437,685 A * | 8/1995 | Blasnik ............ 606/151 |
| 5,507,754 A | 4/1996 | Green et al. |
| 5,549,617 A | 8/1996 | Green et al. |
| 5,562,689 A | 10/1996 | Green et al. |
| 5,603,718 A | 2/1997 | Xu |
| 5,611,515 A | 3/1997 | Benderev et al. |
| 5,628,757 A | 5/1997 | Hasson |
| 5,667,488 A | 9/1997 | Lundquist et al. |
| 5,817,074 A | 10/1998 | Racz |
| 5,840,011 A | 11/1998 | Landgrebe et al. |
| 5,899,909 A | 5/1999 | Claren et al. |
| 5,928,244 A | 7/1999 | Tovey et al. |
| 5,928,252 A | 7/1999 | Steadman et al. |
| 5,934,283 A | 8/1999 | Willem et al. |
| 5,964,732 A | 10/1999 | Willard |
| 6,010,447 A | 1/2000 | Kardjian |
| 6,042,534 A | 3/2000 | Gellman et al. |
| 6,042,536 A | 3/2000 | Tihon et al. |
| 6,056,688 A | 5/2000 | Benderev et al. |
| 6,074,395 A | 6/2000 | Trott et al. |
| 6,110,101 A | 8/2000 | Tihon et al. |
| 6,117,067 A | 9/2000 | Gil-Vernet |
| 6,221,005 B1 | 4/2001 | Bruckner et al. |
| 6,245,082 B1 | 6/2001 | Gellman et al. |
| 6,264,676 B1 | 7/2001 | Gellmann et al. |
| 6,273,852 B1 | 8/2001 | Lehe et al. |
| 6,306,079 B1 | 10/2001 | Trabucco |
| 6,328,686 B1 | 12/2001 | Kovac |
| 6,368,859 B1 | 4/2002 | Atala |
| 6,382,214 B1 | 5/2002 | Raz et al. |
| RE37,815 E | 8/2002 | Rizvi |
| 6,475,139 B1 | 11/2002 | Miller |
| 6,494,887 B1 * | 12/2002 | Kaladelfos ............ 606/148 |
| 6,502,578 B2 | 1/2003 | Raz et al. |
| 6,506,190 B1 | 1/2003 | Walshe |
| 6,575,897 B1 | 6/2003 | Ory et al. |
| 6,575,998 B2 | 6/2003 | Beyar |
| 6,595,911 B2 | 7/2003 | LoVuolo |
| 6,596,001 B2 | 7/2003 | Stormby et al. |
| 6,596,011 B2 | 7/2003 | Johnson et al. |
| 6,612,977 B2 | 9/2003 | Staskin et al. |
| 6,638,210 B2 | 10/2003 | Berger |
| 6,638,211 B2 | 10/2003 | Suslian et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,666,817 B2 | 12/2003 | Li |
| 6,673,010 B2 * | 1/2004 | Skiba et al. ............ 600/37 |
| 6,689,047 B2 | 2/2004 | Gellman |
| 6,691,711 B2 | 2/2004 | Raz et al. |
| 6,752,814 B2 | 6/2004 | Gellman et al. |
| 6,755,781 B2 | 6/2004 | Gellmann |
| 6,755,843 B2 | 6/2004 | Chung et al. |
| 6,802,807 B2 | 10/2004 | Anderson et al. |
| 6,830,052 B2 | 12/2004 | Carter et al. |
| 6,911,003 B2 | 6/2005 | Anderson et al. |
| 6,932,759 B2 | 8/2005 | Kammerer et al. |
| 6,953,428 B2 | 10/2005 | Gellmann et al. |
| 6,960,160 B2 | 11/2005 | Browning |
| 6,971,986 B2 | 12/2005 | Staskin et al. |
| 7,037,255 B2 | 5/2006 | Inman |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,112,171 B2 | 9/2006 | Rocheleau et al. |
| 7,131,943 B2 | 11/2006 | Kammerer |
| 7,175,591 B2 | 2/2007 | Kaladelfos |
| 7,198,597 B2 | 4/2007 | Siegel et al. |
| 7,204,802 B2 | 4/2007 | De Leval |
| 7,261,723 B2 | 8/2007 | Smith et al. |
| 7,267,645 B2 | 9/2007 | Anderson et al. |
| 7,291,104 B2 | 11/2007 | Neisz |
| 7,326,213 B2 | 2/2008 | Benderev et al. |
| 7,338,502 B2 | 3/2008 | Rosenblatt |
| 7,361,138 B2 | 4/2008 | Wagner et al. |
| 7,393,320 B2 | 7/2008 | Montpetit et al. |
| 7,410,460 B2 | 8/2008 | Benderev |
| 7,422,557 B2 | 9/2008 | Arnal et al. |
| 7,500,945 B2 | 3/2009 | Cox et al. |
| 7,556,598 B2 | 7/2009 | Rao |
| 7,611,454 B2 | 11/2009 | De Leval |
| 7,621,864 B2 | 11/2009 | Suslian et al. |
| 7,686,760 B2 | 3/2010 | Anderson et al. |
| 7,713,188 B2 | 5/2010 | Bouffier |
| 7,763,034 B2 | 7/2010 | Siegel et al. |
| 7,794,385 B2 | 9/2010 | Rosenblatt |
| 7,811,223 B2 | 10/2010 | Hodroff et al. |
| 7,828,715 B2 | 11/2010 | Haverfield |
| 2001/0049467 A1 | 12/2001 | Lehe et al. |
| 2004/0230206 A1 | 11/2004 | Gellman et al. |
| 2005/0021086 A1 * | 1/2005 | De Leval ............ 606/222 |
| 2005/0075660 A1 | 4/2005 | Chu et al. |
| 2005/0101834 A1 | 5/2005 | Merade |
| 2005/0245787 A1 | 11/2005 | Cox et al. |
| 2006/0058780 A1 | 3/2006 | Edwards et al. |
| 2006/0063968 A1 | 3/2006 | Anderson et al. |
| 2006/0069301 A1 | 3/2006 | Neisz et al. |
| 2006/0142637 A1 | 6/2006 | Gill |
| 2006/0173468 A1 | 8/2006 | Simmon et al. |
| 2006/0195007 A1 | 8/2006 | Anderson et al. |
| 2006/0217589 A1 | 9/2006 | Wan et al. |
| 2006/0235262 A1 | 10/2006 | Arnal et al. |
| 2006/0258898 A1 | 11/2006 | Montpetit et al. |
| 2006/0293554 A1 | 12/2006 | Crawford |
| 2007/0156012 A1 | 7/2007 | Tracey et al. |
| 2007/0173599 A1 | 7/2007 | Liu et al. |
| 2007/0173864 A1 | 7/2007 | Chu |
| 2007/0249936 A1 | 10/2007 | Deckman et al. |
| 2007/0249939 A1 | 10/2007 | Gerbi et al. |
| 2007/0288046 A1 * | 12/2007 | Grayzel et al. ............ 606/174 |
| 2008/0004487 A1 | 1/2008 | Haverfield |
| 2008/0009914 A1 | 1/2008 | Buysman et al. |
| 2008/0021263 A1 | 1/2008 | Escude et al. |
| 2008/0076963 A1 | 3/2008 | Goria |
| 2008/0082121 A1 | 4/2008 | Chu |
| 2008/0091058 A1 | 4/2008 | Bosley et al. |
| 2008/0097329 A1 | 4/2008 | Hodroff et al. |
| 2008/0154087 A1 | 6/2008 | Wagner et al. |
| 2008/0167520 A1 | 7/2008 | Benderev |
| 2008/0200751 A1 | 8/2008 | Browning |
| 2009/0023978 A1 | 1/2009 | Arnal et al. |
| 2009/0048479 A1 | 2/2009 | Goria |
| 2009/0088599 A1 | 4/2009 | Zook et al. |
| 2009/0137861 A1 | 5/2009 | Goldberg et al. |
| 2009/0137862 A1 | 5/2009 | Evans et al. |
| 2009/0143637 A1 | 6/2009 | Raz et al. |
| 2009/0149700 A1 | 6/2009 | Garcia et al. |
| 2009/0171140 A1 * | 7/2009 | Chu ............ 600/37 |
| 2009/0177026 A1 | 7/2009 | Goldman |
| 2009/0216072 A1 | 8/2009 | Zipper |
| 2009/0221868 A1 | 9/2009 | Evans |
| 2009/0240104 A1 * | 9/2009 | Ogdahl et al. ............ 600/37 |
| 2009/0264698 A1 | 10/2009 | Arnal et al. |
| 2009/0276038 A1 | 11/2009 | Tremulis et al. |
| 2009/0287229 A1 | 11/2009 | Ogdahl |
| 2009/0306464 A1 | 12/2009 | Griguol |
| 2010/0030016 A1 | 2/2010 | Knoll |
| 2010/0113866 A1 | 5/2010 | Goldman |
| 2010/0113867 A1 | 5/2010 | Wiles et al. |
| 2010/0113868 A1 | 5/2010 | Goldman |
| 2010/0191046 A1 | 7/2010 | Gobron et al. |
| 2010/0217069 A1 | 8/2010 | Meade et al. |
| 2010/0261952 A1 | 10/2010 | Montpetit et al. |
| 2010/0324357 A1 | 12/2010 | Chu |
| 2012/0158009 A1 * | 6/2012 | Ostrovsky et al. ............ 606/108 |

OTHER PUBLICATIONS

Invitation to Pay Additional Fees and Partial Search Report for International Application No. PCT/US2012/022944, mailed Apr. 25, 2012, 9 pages.

* cited by examiner

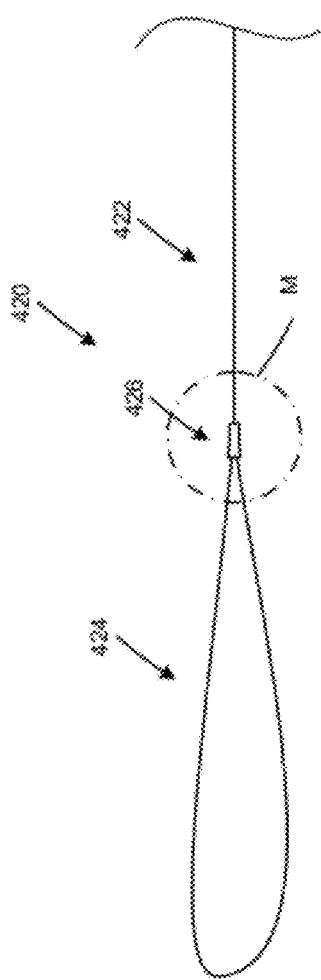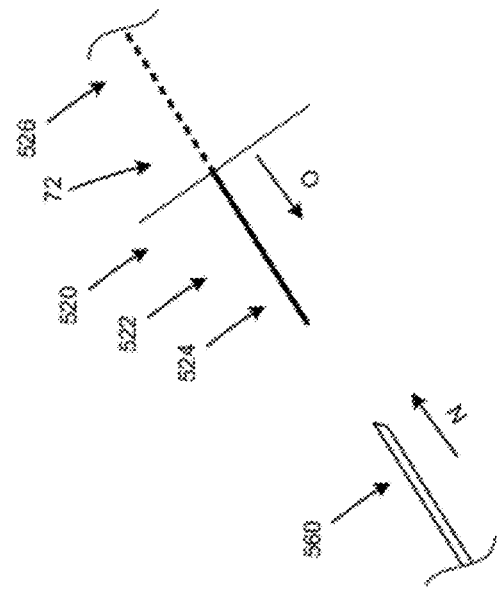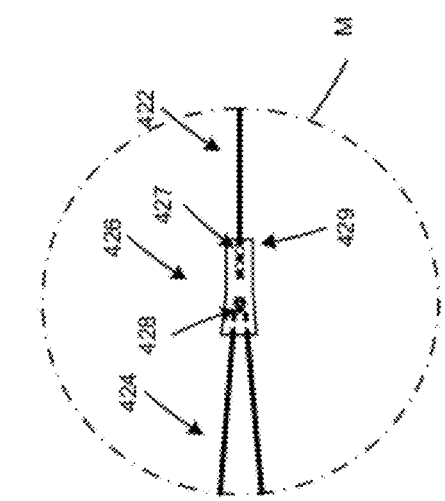
FIG. 4A
FIG. 4B
FIG. 5

DEFLECTION MEMBER FOR DELIVERING IMPLANTS AND METHODS OF DELIVERING IMPLANTS

CROSS REFERENCE TO RELATED APPLICATION

This application is a Nonprovisional of, and claims priority to, U.S. Provisional Application No. 61/437,877, filed on Jan. 31, 2011, entitled "DEFLECTION MEMBER FOR DELIVERING IMPLANTS AND METHODS OF DELIVERING IMPLANTS", which is incorporated by reference herein in its entirety.

TECHNICAL FIELD

This disclosure relates generally to medical devices and more particularly to medical devices that are configured to place or deliver implants within a body of a patient.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some such medical procedures have included placing implants within the pelvic region of the patient. Some of the implants are delivered to the pelvic region of the patient through one or more vaginal incisions, and/or through exterior incisions in the patient.

Often such implants are delivered or placed within the body of the patient using an insertion or delivery tool. The insertion tools used to deliver the implants within a body of a patient typically include a curved portion and a sharp needle or point at one end. Some of the insertion tools used to deliver the implants have large needles that can cause undesirable levels of trauma to tissues during the implantation process. Also some of the insertion tools used to deliver the implants are uncontrollable and can deviate from the desired direction during the implantation process. Accordingly, complications, such as inadvertent nerve, bladder, or uretheral punctures can occur during the implantation process. Such complications can also occur if the shape or curvature of the insertion tool is inappropriate for delivering the implant to the desired location within the body of the patient.

Thus, it would be desirable to provide an insertion tool that may be used to deliver an implant to a location within a body of a patient without damaging tissue and/or adjacent nerves or organs in an undesirable fashion.

SUMMARY

In one general aspect, an apparatus can include an elongate member configured to be associated with an implant and having a piercing portion. The apparatus can include a deflection member having a fixed curvature disposed within a plane. The deflection member can have a distal end configured to be disposed within a body of a patient. The deflection member can define a groove extending along at least a portion of the deflection member. The groove of the deflection member can be configured to deflect the piercing portion of the elongate member.

BRIEF DESCRIPTION OF THE DRAWINGS

FIG. 4A illustrates a portion of an elongate member, according to an embodiment.

FIG. 4B is a zoomed-in view of the connector of the elongate member shown in FIG. 4A.

FIG. 5 illustrates an injection needle configured to inject a fluid into a passageway associated with an elongate member, according to an embodiment.

DETAILED DESCRIPTION

Figure 1A:
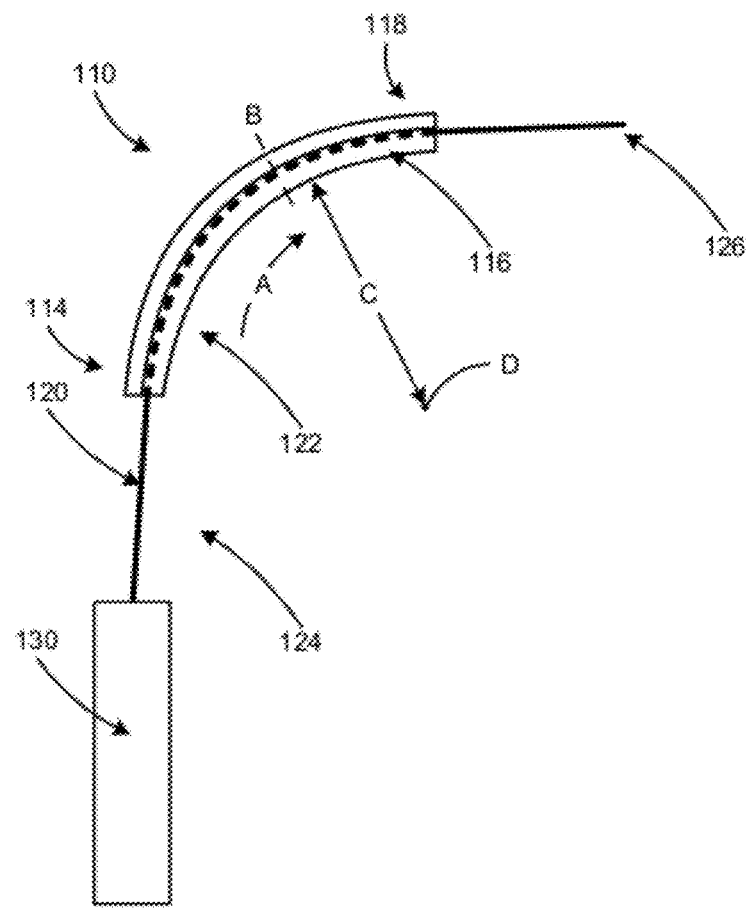
FIGS. 1A and 1B are schematic diagrams of a deflection member 110, according to an embodiment.

The devices and methods described herein are generally directed to insertion or delivery tools for placing implants within a body of a patient. The implants delivered with the insertion or delivery tools may be used in any portion of a body of a patient. In some embodiments, the implants include, but are not limited to, implants that are placed within a pelvic region of a patient. For example, the implants that may be placed with the disclosed insertion or delivery tools include posterior support implants, anterior support implants, and total pelvic floor repair implants. Such implants can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. The insertion tools, implants, and procedures described herein may be used in a female patient or a male patient.

In some embodiments, the disclosed insertion or delivery tool may be used to place an implant, for example, through a vaginal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or posterior vaginal incision. In some embodiments, a procedure may include an exterior incision.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of an insertion tool or device as described herein refers to the end or portion of the device that is first inserted into a body of a patient during a medical procedure. The proximal end or portion is the end or portion of the device that is remains outside of the body of the patient during the insertion procedure (or if the entire device is inserted into the body of the patient during the delivery procedure, the proximal end portion is inserted into a body of the patient after the distal end or distal portion is inserted). The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that remains outside of the body of the patient or is inserted into the body after the leading end.

Various embodiments of insertion or delivery tools are described herein. The insertion or delivery tool may be used to deliver a variety of different implants into the body of a patient and only some examples of implants are described herein.

Figure 1B:
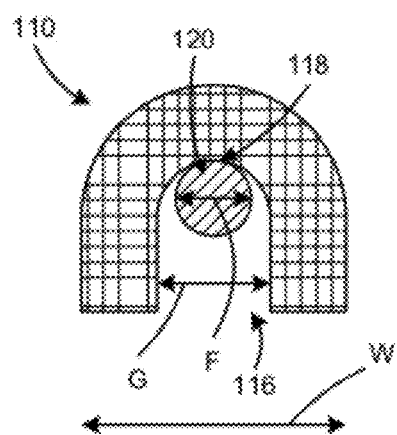

FIGS. 1A and 1B are schematic diagrams of a deflection member 110, according to an embodiment. The deflection member 110 is configured to be used as an insertion tool or delivery tool to implant or insert an implant 130 (e.g., a bodily implant) into a body of a patient. In some embodiments, the deflection member 110 can be configured to place the implant 130 into a pelvic region of a patient. Specifically, in some embodiments, the deflection member 110 is configured to place the implant 130 through an obturator muscle or a membrane of a patient. In some embodiments, the implant 130 is referred to as a surgical implant, or as a bodily implant.

As shown in FIG. 1A, the deflection member 110 is configured to deflect an elongate member 120 when the elongate member 120 is slidably moved (e.g., advanced) within a groove 116 defined by and extending along the deflection member 110 along direction A. Specifically, the elongate member 120 is deflected along a curvature defined by the groove 116 of the deflection member 110. In some embodiments, the deflection member 110 is referred to as a guide or as a grooved guide. Although not shown in FIG. 1A, in some embodiments, the elongate member 120 may be slidably moved (e.g., retracted) in a direction opposite direction A.

In some embodiments, the elongate member 120 can be any type of elongate member that can be deflected by the deflection member 110 and coupled to the implant 130. As shown in FIG. 1A, the elongate member 120 has a proximal portion 124 associated with the implant 130. For example, the elongate member 120, which can have a flexible wire or flexible needle, can be associated with (e.g., coupled to) implant 130 and can be deflected by the deflection member 110. In some embodiments, the distal end 126 of the elongate member 120 is configured to cut or pierce a bodily tissue. For example, in some embodiments, the distal end 126 includes a sharp portion (e.g., a sharp portion at a distal tip). In some embodiments, the distal end 126 of the elongate member 120 defines a blunt end.

As shown in FIG. 1A, the curvature of the deflection member 110 can be uniform about a radius C. As shown in FIG. 1A, the deflection member 110 has a centroid D. Thus, the elongate member 120 is configured to be deflected by the deflection member 110 around the centroid D and along a curvature with the radius C. As shown in FIG. 1A, the groove 116 of the deflection member 120 faces the centroid D.

In some embodiments, the radius C of the curvature of the deflection member 110 can be fixed. In other words, the radius C of the curvature of the deflection member 110 from approximately the distal end 118 of the deflection member 110 to the proximal end 114 of the deflection member 110 can be uniform or constant (e.g., relatively uniform, relatively constant). In some embodiments, the radius C of curvature of the deflection member 110 can be approximately 3 cm. In some embodiments, the radius C of curvature of the deflection member 110 can be greater than 3 cm (e.g., 3.3 cm, 5 cm, 10 cm), or can be less than 3 cm (e.g., 2.5 cm, 1 cm). In some embodiments, the deflection member 110 can define an arc of approximately 120 degrees. In some embodiments, the deflection member 110 can define an arc that is greater than 120 degrees (e.g., 130 degrees, 160 degrees), or an arc that is less than 120 degrees (e.g., 110 degrees, 90 degrees, 50 degrees).

In some embodiments, the radius of the curvature of the deflection member 110 varies. In other words, in some embodiments, the deflection member 110 may not have a uniform radius of curvature. In some embodiments, the radius of the curvature of the curved portion of the deflection member 110 varies from the distal end 118 to the proximal end 114 of the deflection member 110. In other words, in some embodiments, the curved portion may not have a uniform radius of curvature. An example of a deflection member with a non-uniform radius of curvature is shown and described in connection with FIG. 7.

In some embodiments, the deflection member 110 is made of a relatively rigid material configured to deflect the elongate member 120 without flexing the deflection member 110 (or inelastically bending the deflection member 110). In some embodiments, the deflection member 110 is made of one or more biocompatible materials. In some embodiments, the deflection member 110 is monolithically formed from a biocompatible material. For example, in some embodiments, the deflection member 110 is injection molded from a polymer-based material. In some embodiments, the deflection member 110 is made out of (e.g., cut from) any type of metal such as stainless steel (e.g., stainless steel sheet-metal). For example, a straight grooved piece of metal can be bent to a desired curvature to form the deflection member 110 shown in FIG. 1A. In some embodiments, the deflection member 110 is made of multiple pieces of material (multiple pieces of metal) that are coupled together (e.g., welded together).

In some embodiments, the distal end 118 of the deflection member 110 is configured to cut or pierce a bodily tissue. Although not shown in FIG. 1A, in some embodiments, the distal end 118 includes a sharp portion (e.g., a sharp portion at a distal end). In some embodiments, the distal end 118 defines a blunt end. In some embodiments, the distal end 118 can define a dilating end configured to dilate a tissue of a patient.

FIG. 1B is a schematic diagram that illustrates a zoomed-in cross-sectional view of the groove 116 of the deflection member 110 shown in FIG. 1A cut at line B. As shown in FIG. 1B, the groove 116 is open so that at least a portion of the elongate member 120 is exposed to an ambient environment around the deflection member 110. Thus, in some embodiments, the groove 116 is referred to as an open groove. As shown in FIG. 1B, the groove 116 in this embodiment defines an upside-down U-shape. The deflection member 110 defines the groove 116 within which the elongate member 120 is disposed. The elongate member 120 slidably moves against an inner surface 118 of the deflection member 110 that defines the groove 116.

In some embodiments, the deflection member 110 has a width W that is approximately the same as a width of an implant (not shown). In some embodiments, the width W of the deflection member 110 is less than a centimeter (e.g., approximately 0.2 centimeters). In some embodiments, the width W of the deflection member 110 is greater than a centimeter. In some embodiments, the deflection member 110 has a width W that is less than that of an implant, or greater than that of an implant.

In some embodiments, the groove 116 has a shape that is different than the upside-down U shape shown in FIG. 1B. In some embodiments, the groove 116 of the deflection member 110 has a cross-sectional shape (or outer profile) of any type of polygon. For example, the groove 116 can have a square or rectangular cross-sectional shape (or outer profile) within which the elongate member 120 can be disposed. In some embodiments, the groove is a V-shape, a C-shape, and/or so forth. In some embodiments, the groove 116 has any shape within which the elongate member 120 can be guided. In some embodiments, the groove 116 functions as a channel or track along which the elongate member 120 may be moved.

Figure 14:
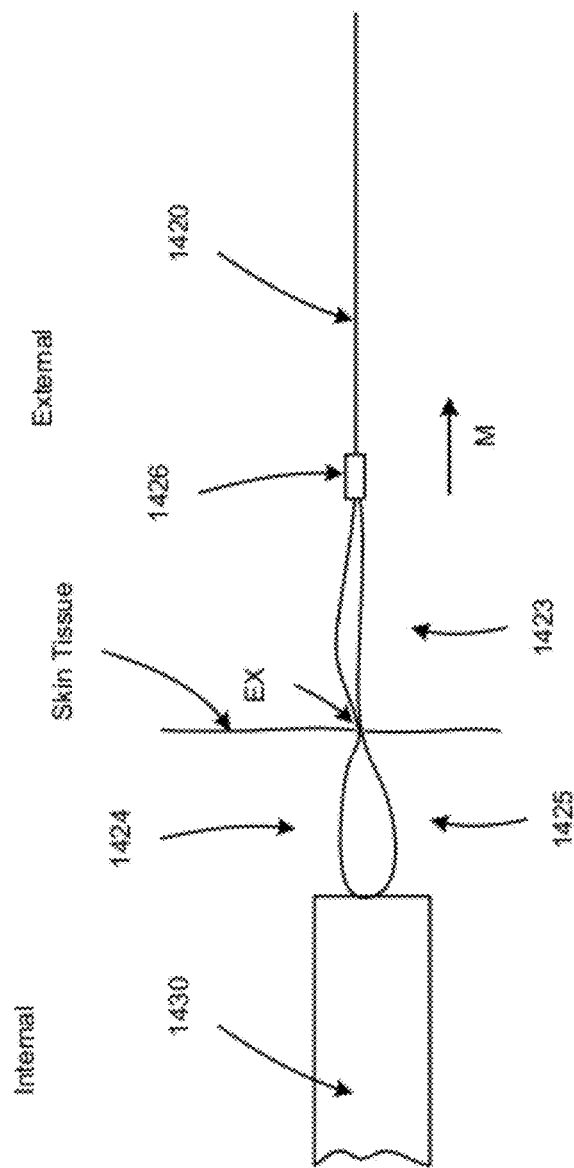
FIG. 14 illustrates another implant disposed within a body of a patient.
Figure 15:
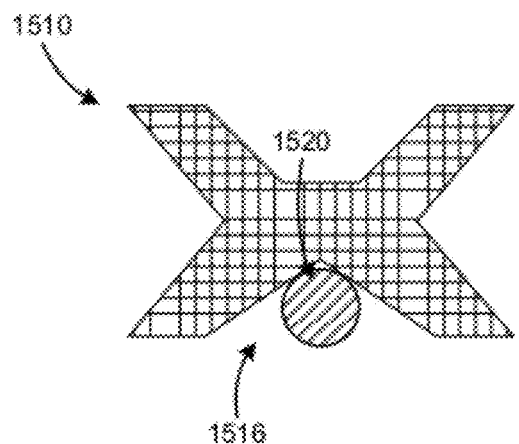
FIG. 15 illustrates a zoomed-in cross-sectional view of a deflection member that has an X-shaped cross section.

In some embodiments, the cross-sectional shape of the deflection member 110 can be, for example, an X-shape, an I-shape, an H-shape and/or so forth. In such embodiments, the cross-sectional shape of the deflection member 110 facilitates the structural integrity of the deflection member 110. In other words, the cross-sectional shape of the deflection member 110 provides strength so that, for example, the curvature (e.g., the structural integrity of the curvature) of the deflection member 110 along the length of the deflection member 110 (from the proximal end 114 to the distal end 118 shown in FIG. 1A) may be maintained. Examples of deflection members with different cross-sectional shapes are shown in FIGS. 14 and 15.

As shown in FIG. 1B, the elongate member 120 has a circular cross-sectional shape (where the cross-section is approximately orthogonal to a longitudinal axis of the elongate member 120). In some embodiments, the elongate member 120 has a cross-sectional shape of any type of polygon. For example, the elongate member has a square or rectangular cross-sectional shape (or outer profile).

As shown in FIG. 1B, a diameter F of the elongate member 120 is smaller than a width G of the groove 116. The width G of the groove 116 is shown as a distance between an internal surface of a first sidewall of the deflection member 110 and an internal surface of a second sidewall the deflection member 110. In some embodiments, the diameter F of the elongate member 120 may be significantly smaller than the width G of the groove 116.

In some embodiments, the width G of the groove 116 can be a few centimeters (cm) (e.g., 1 cm, 2 cm) or less than a few centimeters (e.g., 0.5 cm). If used to place the implant 130 via an obturator, the elongate member 120 can have a length of approximately 20 cm. In some embodiments, the elongate member 120 can have a length less than 20 cm (e.g., 15 cm, 10 cm) or a length greater than 20 cm (e.g., 25 cm, 30 cm).

In some embodiments, the elongate member 120 may have a tapered shaped and/or a tapered portion (e.g., tapered along a longitudinal axis of the elongate member 120 towards a distal end of the elongate member 120). In such embodiments, the tapered shape may facilitate dilation of tissue when being inserted into the tissue of a patient. In some embodiments, the elongate member 120 can have a diameter of approximately one millimeter (mm). In some embodiments, the elongate member 120 can have a diameter less than one millimeter (mm) (e.g., 0.5 mm, 0.8 mm). In some embodiments, the elongate member 120 can have a diameter greater than one millimeter (e.g., 1.5 mm, 2 mm). In some embodiments, an elongate member such as elongate member 120 can be associated with each end of the implant 130, and each of the elongate members may be used to insert different ends of the implant 130 into a body of a patient.

Referring back to FIG. 1A, in some embodiments, the deflection member 110, the elongate member 120, and the implant 130 are included in a kit that can be used by, for example, a physician. In some embodiments, the deflection member 110 and the elongate member 120 can be included in the kit. In some embodiments, the elongate member 120 and the implant 130 can be included in a kit. In some embodiments, any of the kits described above may be used for an inside-out implant approach (e.g., transobturator approach) and/or an outside-in implant approach.

In some embodiments, the deflection member 110 and the groove 116 have a uniform (or substantially uniform) cross-sectional shape (or outer profile) from the proximal end 114 to the distal end 118. In some embodiments, the deflection member 110 and/or the groove 116 may not have a uniform (or substantially uniform) cross-sectional shape (or outer profile) from the proximal end 114 to the distal end 118. In other words, the deflection member 110 and/or the groove 116 may have a cross-sectional shape (or outer profile) that varies between the proximal end 114 and the distal end 118. For example, in some embodiments, the deflection member 110 and/or the groove 116 may have a tapered shaped and/or a tapered portion (e.g., tapered from the proximal end 114 to the distal end 118). Specifically, a width of the groove 116 may taper from the proximal end 114 of the deflection member 110 to the distal end 118 of the deflection member.

Although not shown, in some embodiments, the deflection member 110 has at least a portion that defines a lumen within which the elongate member 120 may be disposed. The deflection member 110 may define a lumen at the proximal end 114 of the deflection member, at the distal end 118 of the deflection member 110 and/or at a portion between the proximal end 114 and the distal end 118. In such embodiments, the elongate member 120 may be configured to slidably move through the lumen defined by the deflection member 110 when the elongate member 120 is advanced along direction A.

As shown in FIG. 1A, the groove 116 extends along the entire length of the deflection member 110 from the proximal end 114 to the distal end 118. Although not shown in FIG. 1A, in some embodiments, the groove 116 may not extend along the entire length of the deflection member 110. An example of such an embodiment is shown in FIG. 2.

Figure 2:
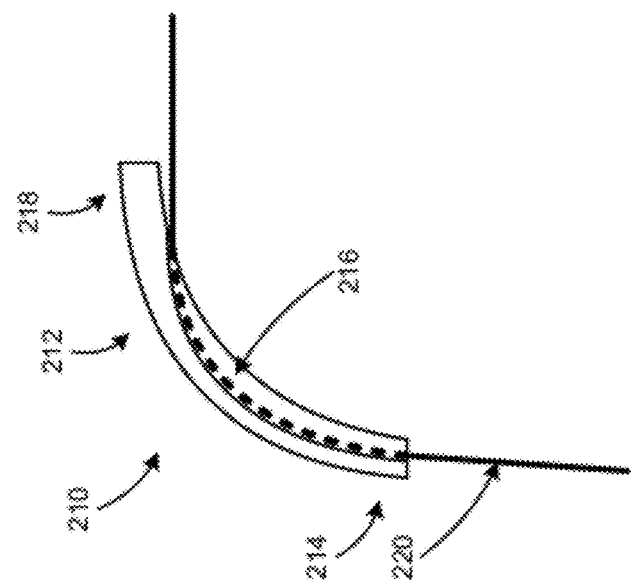
FIG. 2 is a schematic diagram that illustrates a deflection member that has a groove extending along less than all of the length of the deflection member.

FIG. 2 illustrates a deflection member 210 that has a groove 216 extending along less than all of the length of the deflection member 210. In this embodiment, the groove 216 extends from a proximal end 214 of the deflection member 210 to a medial portion 212 of the deflection member 210 and does not extend to a distal end 218 of the deflection member 210. As shown in FIG. 2, an elongate member 220 is deflected out of the groove 216 and away from the deflection member 210 before reaching the distal end 218 of the deflection member 210.

Although not shown in FIG. 2, in some embodiments, the groove 216 is disposed within only the medial portion 212 the deflection member 210. Also, although not shown in FIG. 2, in some embodiments, the groove 216 may extend from the medial portion 212 of the deflection member 210 to the distal end 218 of the deflection member 210 and may not extend to the proximal end 214 of the deflection member 210.

Referring back to FIG. 1A, as mentioned above, in some embodiments, the deflection member 110 and the elongate member 120 may be used to insert the implant 130 into a body of a patient. In some embodiments, the distal end 118 of the deflection member 110 is inserted into a pelvic region of the patient through, for example, an anterior vaginal incision (i.e., via an inside-out approach). In some embodiments, the deflection member 110 is inserted into the pelvic region of the patient so that the distal end 118 of the deflection member 110 is in a position on one side of an incision (e.g., on one side of a tissue via the incision) in the proximal end 114 of the deflection member is in a position on another side of the incision (e.g., on another side of the tissue via the incision). Accordingly, the deflection member 110 is held in place by tissue of the patient.

After the deflection member 110 has been inserted into the pelvic region of the patient in a desirable location, the elongate member 120 (or a portion thereof) is slidably moved along the deflection member 110 so that at least a portion of the implant 130 attached to the proximal portion 124 of the elongate member 120 is moved into the body of patient in a specified location. In some embodiments, the distal end 126 of the elongate member 120 is moved through a tissue of the patient so that the implant 130, which is attached to the elongate member 120, is placed within the tissue of the patient. In some embodiments, the distal end 126 of the elongate member 120 may exit the body of the patient, and the distal end 126 (or distal portion) of the elongate member 120 may be pulled (e.g., pulled by a physician) so that the implant 130, which is associated with the proximal portion 124 of the elongate member 120, is moved into a desirable location within the body of the patient.

In some embodiments, the implant 130 is associated with (e.g., attached to) the proximal portion 124 of the elongate member 120 after at least a medial portion 122 of the elongate member 120 has been slidably moved along the deflection member 110 and has been disposed (e.g., disposed at a position) within the body of the patient. In some embodiments, the portion of the elongate member 120 disposed within the body of the patient via the deflection member 110 is at least a piercing portion that is a wire or needle, and the implant 130 may be coupled to the wire via a tether portion and connector (which can be considered part of an assembly of the elongate member 120) after the wire or needle has the portion disposed within the body of the patient. In some embodiments, the distal end 126 of the elongate member 120 may have already exited (e.g., may be disposed outside of) the body of the patient when the implant 130 is associated with (e.g., coupled to) the proximal portion 126 of the elongate member 120 (using a tether portion and connector). More details related to the assembly of the elongate member 120 are described in connection with FIGS. 4A and 4B.

In some embodiments, after at least a portion (e.g., the medial portion 122) of the elongate member 120 has been disposed (e.g., disposed at position) within the body of the patient, the deflection member 110 (e.g., the distal end 118 of the deflection member 110) may be removed (e.g., withdrawn) from the body of the patient. Thus, the portion of elongate member 120 may remain (e.g., remain at a position) within the body of the patient even though the deflection member 110 is removed from the body of the patient. In some embodiments, the deflection member 110 is removed without interfering with the portion of the elongate member 120 (and/or the implant 130 if the implant is already associated with the portion of the elongate member 120). In some embodiments, the deflection member 110 may be removed after the distal end 126 of the elongate member 120 has exited the body of the patient. In some embodiments, the implant 130 is associated with the proximal portion 126 of the elongate member 120 before, or after, the deflection member 110 has been removed from the body of the patient.

As another specific example, in some embodiments, the deflection member 110 is inserted towards, and up to (but not through), an obturator muscle and/or membrane of a patient via an anterior vaginal mid-line incision. In some embodiments, the deflection member 110 is inserted into the patient using, for example, a hemostat (not shown in FIG. 1A). After the deflection member 110 has been inserted via the midline incision, the hemostat is removed and the deflection member 110 is held in place by tissue of the patient. While the deflection member 110 is being held in place by the tissue of the patient, the elongate member 120 is slidably moved along the deflection member 110. In some embodiments, the deflection member 110 may be configured to deflect the elongate member 120 so that the elongate member 120 is close to, for example, the ischio pubic ramus, but does not contact lateral nerves of the patient. In some embodiments, the distal end 126 of the elongate member 120 is moved through the obturator muscle and/or membrane of the patient and outside of the body of the patient. The implant 130, which may be associated with (e.g., coupled to, attached to) the proximal portion 124 (or distal end 126) of elongate member 120 before or after the elongate member 120 is disposed within the body of the patient, may be placed within or near the obturator muscle and/or membrane tissue of the patient by pulling the elongate member 120 in a direction away from the body of the patient.

Although not shown in FIG. 1A, in some embodiments, an implant (such as implant 130) may have more than one portion that may be inserted into a body of a patient using multiple deflection members (such as deflection member 110) and multiple elongate members (such as elongate member 120). For example, a first deflection member may be inserted into a first incision within a body of a patient, and a second deflection member may be inserted into a second incision (or into the first incision) within the body of the patient. In such embodiments, the first deflection member has a groove that faces in a different direction than a groove of the second deflection member. In some embodiments, the groove of the first deflection member faces a first side of the patient, and the groove of the second deflection member faces a second side (i.e., a contralateral side) of the patient.

After the deflection members have been inserted, a first elongate member, which may be attached to a first portion of the implant, may be slidably moved along the first deflection member so that the first portion of the implant (which may coupled to the elongate member after at least a portion of the elongate member has been deflected and disposed within the body of the patient) may be placed within the body of the patient via the first incision. A second elongate member, which may be attached to a second portion of the implant. may be slidably moved along the second deflection member so that the second portion of the implant (which may coupled to the elongate member after at least a portion of the elongate member has been deflected and disposed within the body of the patient) may be placed within the body of the patient via the second incision (or via the first incision).

In some embodiments, the same elongate member (rather than two different elongate members) may be used during the procedure described above. In some embodiments, at least some portions of insertion (described above) of the first portion of the implant and the second portion of the implant may be performed concurrently. In some embodiments, a single incision (e.g., an anterior vaginal incision, a midline incision) may be used during the implantation procedure for an inside-out approach, and multiple incisions (e.g., multiple skin incisions, a suprapubic skin incision, a skin incision proximate the obturator foramen) may be used during the implantation procedure for an outside-in approach.

Although not shown in FIG. 1A, in some embodiments, an implant (such as implant 130) may have more than one portion that may be inserted into a body of a patient using a single deflection member (such as deflection member 110) and one or more elongate members (such as elongate member 120). For example, a deflection member may be inserted into an incision (e.g., an anterior vaginal incision, a midline incision) within a body of a patient. The deflection member has a groove facing a first side of the patient. An elongate member, which may be attached to a first portion of the implant, may be slidably moved along the deflection member so that the first portion of the implant (which may coupled to the elongate member after at least a portion of the elongate member has been deflected and disposed within the body of the patient) may be placed within the body of the patient via the incision. After the first portion of the implant has been placed within the body of the patient, the deflection member may be rotated within the incision. Alternatively, the deflection member may be removed from the body of the patient via the incision, rotated, and then reinserted in a different orientation within the incision. In such instances, the groove defined by the deflection member, after being rotated within or outside of the incision, will face a second side (i.e., a contralateral side) of the body of the patient. The elongate member (or another elongate member), which may be attached to a second portion of the implant, may be slidably moved along the deflection member so that the second portion of the implant (which may be coupled to the elongate member after at least a portion of the elongate member has been deflected and disposed within the body of the patient) may be placed within the body of the patient via the incision.

Figure 3B:
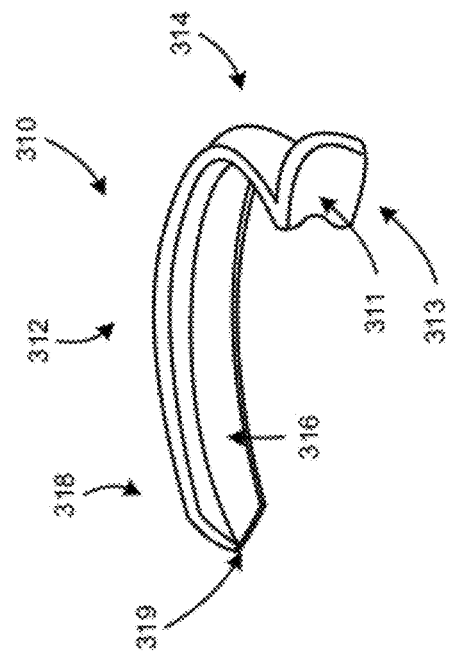
FIG. 3B is a perspective view of the deflection member shown in FIG. 3A.
Figure 3A:
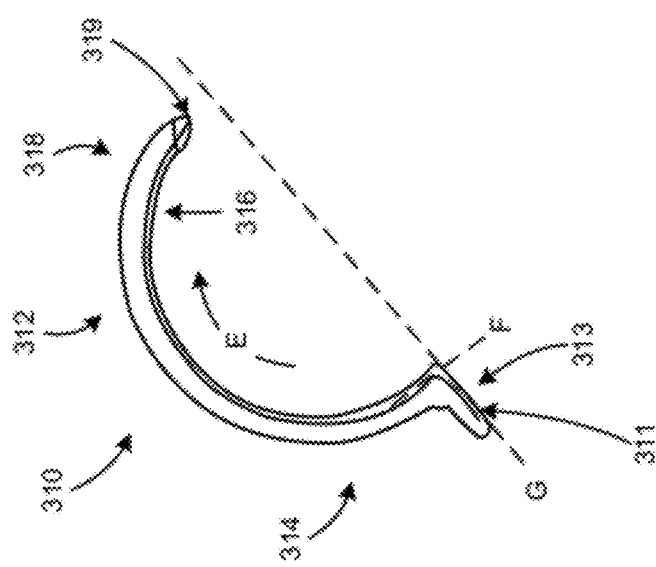
FIG. 3A is a side view of a deflection member, according to an embodiment.

FIG. 3A is a schematic diagram that illustrates a side view of a deflection member 310, according to an embodiment. The deflection member 310 has a distal tip 319 at a distal end 318 configured to pierce a tissue of the body of the patient, and a tab 313 at a proximal end 314. In some embodiments, the tab 313 is used to position the deflection member 310 within a body of a patient. Specifically, the tab 313 may be a portion of the deflection member 310 that may be grasped by a physician using, for example, a tool (e.g., a hemostat) and moved to a desirable location within a body of patient. In some embodiments, the tab 313 may not be disposed at an end of the deflection member 310. In other words, the tab 313 may be disposed in a medial portion of the deflection member 310. In some embodiments, the tab 313 may be referred to as a tab portion of the deflection member 310.

As shown in FIG. 3A, the tab 313 is aligned along (or has a base surface 311 aligned along) an axis G or has a base surface 311 disposed within a plane (which extends out of the page and is not shown) aligned along axis G that is orthogonal (or approximately orthogonal) to an axis F along which the proximal end 314 of the deflection member 310 is aligned. In this embodiment, the base surface 311 of the tab 313 is disposed within the plane (which extends out of the page) aligned along axis G that is non-parallel to a plane (within the surface of the page) within which the curved portion of the deflection member 310 is disposed. Although not shown in FIG. 3A, in some embodiments, the tab 313 is aligned along an axis that is not orthogonal to the axis F, but is non-parallel to the axis F. Although not shown, in some embodiments, a handle is coupled to the deflection member 310 in addition to, or in lieu of the tab 313.

In this embodiment, the distal end 318 of the deflection member 310 does not extend beyond the axis G along which the tab 313 is aligned. In some embodiments, the distal end 318 of the deflection member 310 extends beyond the axis G along which the tab 313 is aligned. In some embodiments, the distal tip 319 of the deflection member 310 is at the axis G along which the tab 313 is aligned.

An elongate member (such as elongate member 120 shown in FIG. 1), or portion thereof, may be slidably moved within a groove 316 of the deflection member 310 along direction E. In some embodiments, the elongate member (or portion thereof) may be slidably moved in a direction opposite direction E. An example of an elongate member within the groove 316 of the deflection member 310 is shown in connection with FIG. 3C.

FIG. 3B illustrates another view of the deflection member 310 shown in FIG. 3A, according to an embodiment. As shown in FIG. 3B, the groove 316 is a V-shaped groove within which an elongate member can be slidably moved. As shown in FIG. 3B, the groove 316 extends from the distal end 318 of the deflection member 310 to the proximal end 314 of the deflection member 310.

In this embodiment, the groove 316 extends into the distal tip 319 of the deflection member 310. In other words, the deflection member 310 includes or defines the distal tip 319 so that it includes the groove 316, or so that the distal tip 319 defines at least a portion of the groove 316. Similarly, the groove 316 extends into the tab 313 of the deflection member 310. In other words, the deflection member 310 defines the groove 316 so that it includes the tab 313, or so that the tab 313 defines at least a portion of the groove 316.

Figure 3D:
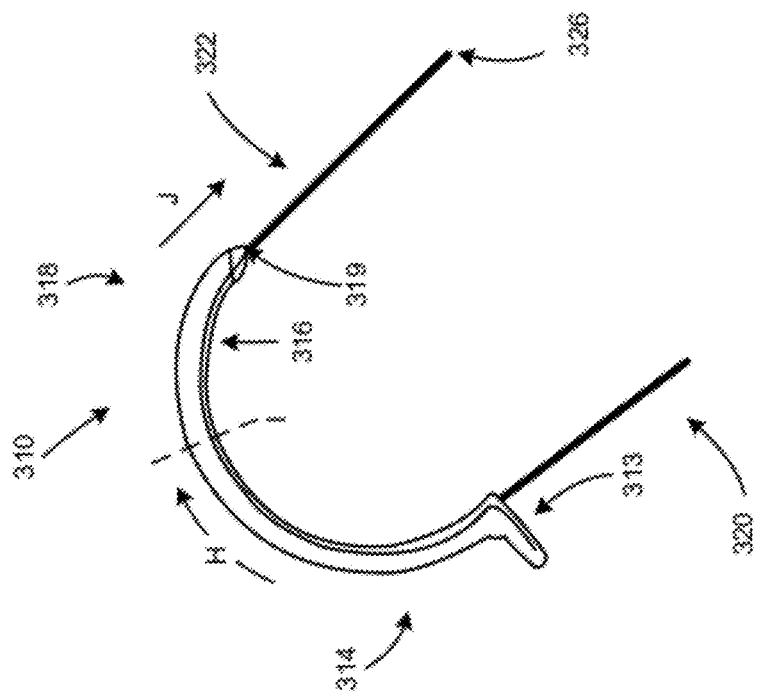
FIG. 3D illustrates the elongate member (shown in FIG. 3C) disposed within a side view of the deflection member.
Figure 3C:
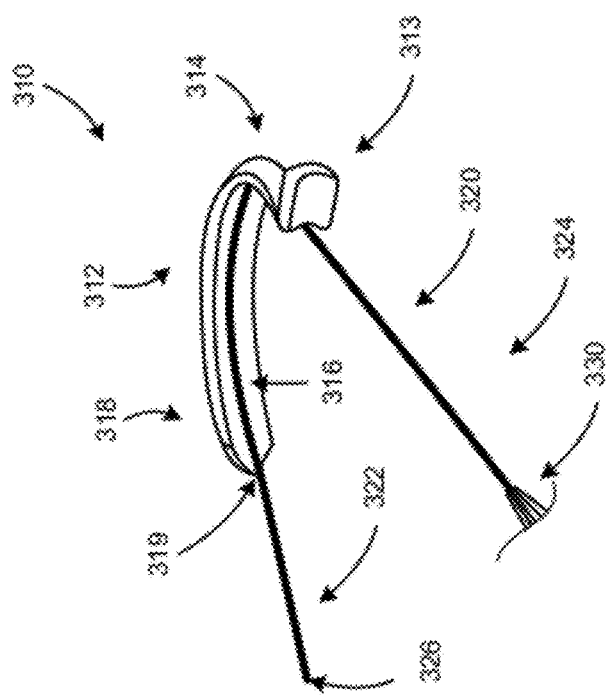
FIG. 3C illustrates an elongate member disposed within the deflection member shown in FIGS. 3A and 3B.

FIG. 3C illustrates an elongate member 320 disposed within the deflection member 310 shown in FIGS. 3A and 3B. Specifically, the elongate member 320 is disposed within the groove 316 of the deflection member 310 so that the elongate member 320 extends along the entire length of the groove 316. As shown in FIG. 3C, the elongate member 320 is deflected by the deflection member 310. In this embodiment, the elongate member 320 is coupled to at least a portion of an implant 330.

The elongate member 320, in some embodiments, is inserted into the groove 316 at the proximal end 314 of the deflection member 310 where the tab 313 is located. The elongate member 320 may be slidably moved within the groove 316 until a distal end 326 of the elongate member 320 moves out of the groove 316 at the distal end 318 of the deflection member 310.

As shown in FIG. 3C, a portion 322 of the elongate member 320 that is disposed outside of the groove 316 of the deflection member 310 is straight (is aligned along a line). The portion 322 is aligned along a tangent from the distal end 318 of the deflection member 310. Because the portion 322 of the elongate member 320 is straight, the portion 322 may have sufficient strength (e.g., sufficient column strength) to pierce a tissue of the body of a patient.

Because certain tissues of a patient (e.g., an obturator muscle) can be relatively stiff and/or relatively difficult to pierce, the deflection member 310 can function as a support for the elongate member 320 as the distal end 326 is moved through the tissues. Because the deflection member 310 can function as a support for the elongate member 320, the elongate member 320 can have a cross-sectional area that is smaller than would otherwise be permissible without the deflection member 310. In other words, the elongate member 320 can be relatively thin (e.g., can have a relatively small diameter) because only a relatively short portion (shown as the portion 322) of the elongate member 320 may project from the deflection member 310.

In some embodiments, the distal end 318 of the deflection member 310 can be moved so that the distal end 318 is contacting or is close to (e.g., less than 2 mm, less than 2 cm) a tissue through which the distal end 326 of the elongate member 320. Because the distal end 318 of the deflection member 110 can be contacting or close to the tissue that will be pierced by the distal end 326 of the elongate member 320, the rigidity of the elongate member 320 can be less than might otherwise be necessary when the distal end 326 is projecting over a relatively long distance (e.g., over 5 cm, over 10 cm) without support from the deflection member 310.

As shown in FIG. 3C, the portion 322 and a portion 324 are disposed within a common plane (plane not shown). The curved portion of the deflection member 310 is also disposed within the same plane. Although not shown in FIG. 3C, in some embodiments, the deflection member 310 may have cork screw or a helical shape so that when the elongate member 320 is disposed within the groove 316 of the deflection member 310, the portion 322 is disposed within a plane that is different from (e.g., non-parallel with) a plane within which the portion 324 is disposed. In such embodiments, the groove 316 of the deflection member 310 may define a twisted shape along the length of the deflection member 310.

FIG. 3D illustrates the elongate member 320 (shown in FIG. 3C) disposed within a side view of the deflection member 310. In this embodiment, the deflection member 310 is shown as being disposed within (e.g., through) a tissue I of a patient (represented by a dashed line). As shown in FIG. 3D, the portion 322 of the elongate member 320 exits the groove 316 of the deflection member 310 at a tangent J. In some embodiments, the direction of the tangent J with respect to the tissue I is changed when the deflection member 310 is moved along direction H (or in a direction opposite direction H). In some embodiments, the deflection member 310 is moved along direction H (or in a direction opposite direction H) using the tab 313. By doing so, the portion 322 (and tip 326) of the elongate member 320 may be directed within a body of patient in a specified direction (e.g., a specified tangential direction). The curvature of the deflection member 310 may be defined so that the portion 322 is directed (along direction J) close to, for example, the ischio pubic ramus and away from lateral nerves of a patient.

Figure 3E:
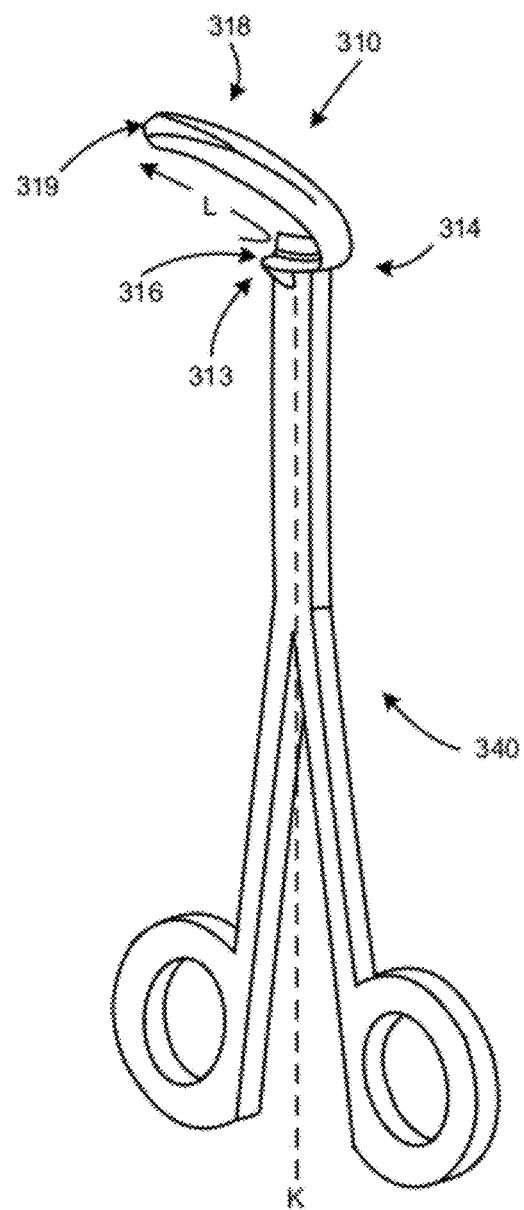
FIG. 3E is a perspective view of a hemostat coupled to the deflection member shown in FIGS. 3A through 3D.

FIG. 3E illustrates a hemostat 340 coupled to the deflection member 310 shown in FIGS. 3A through 3D. In some embodiments, the hemostat 340 is a locking hemostat. As shown in FIG. 3E, the hemostat 340 is coupled to the tab 313 of the deflection member 310. The hemostat 340 is coupled to the tab 313 so that an elongate member (such as elongate member 320 shown in FIGS. 3C and 3D) may be moved into the groove 316 (and slidably moved) without being obstructed by any portion of the hemostat 340.

As shown in FIG. 3E, the deflection member 310 has a curvature L disposed within a plane that is not aligned along a longitudinal axis K of the hemostat 340. In some embodiments, the curvature L of the deflection member 310 is disposed within a plane that is orthogonal to (or substantially orthogonal to) the longitudinal axis K of the hemostat 340. In some embodiments, the deflection member 310 is attached to or clamped relative to the longitudinal axis K of the hemostat 340 in a variety of positions. In some embodiments, the deflection member 310 is coupled to the hemostat 340 such that the curvature L of the deflection member 310 is disposed within a plane that is aligned along the longitudinal axis K. Such an orientation can be referred to as a BSC Obtryx Curve type orientation.

FIG. 4A illustrates a portion of an elongate member 420, according to an embodiment. As shown in FIG. 4A, the elongate member 420 includes a piercing portion 422 coupled to a tether portion 424 (which includes a tether loop) via a connector 426. The tether portion 424 is configured to be coupled to an implant (not shown). The connector 426, in some embodiments, is associated with (e.g., fixedly coupled to) the piercing portion 422 of the elongate member 420, and in other embodiments, the connector 426 is associated with (e.g., fixedly coupled to) the tether portion 424 of the elongate member 420. In some embodiments, the connector 426 is associated with neither the tether portion 424 nor the piercing portion 422 of the elongate member 420. In some embodiments, the tether portion of the elongate member 420 and the piercing portion 422 of the elongate member 420 collectively define an assembly of the elongate member 420.

Although shown in FIG. 4A as being coupled together, in some embodiments the piercing portion of the elongate member 420 may be separate from the tether portion of the elongate member 420 when the piercing portion of the elongate member 420 is inserted within a body of a patient and deflected within a groove of a deflection member. In such embodiments, the tether portion of the elongate member 420 (which may be associated with an implant) may be coupled to the piercing portion of the elongate member 420 after piercing portion of the elongate member has been disposed within a body of patient.

The piercing portion 422 can be made of a relatively flexible material such as a wire or needle that can be deflected by a deflection member (not shown) (such as the deflection members described above). In some embodiments, the piercing portion 422 is made of any biocompatible metal or polymer such as stainless steel or nitinol. In some embodiments, the piercing portion is made of multiple types of materials (e.g., the combination of materials). In some embodiments the piercing portion is monolithically formed so that the piercing portion 422 is made of a single type of material. In some embodiments, the piercing portion 422 is a guide wire with a coil wrapped around a central core. In some embodiments, the central core can be made of, for example, Teflon. In some embodiments the piercing portion 422 is painted with a color (e.g., blue, red).

In some embodiments, the piercing portion 422 has a circular cross-sectional shape and a constant diameter along the length of the piercing portion 422. In some embodiments, the piercing portion 422 has a cross-sectional shape (or outer profile) of any type of polygon. For example, in some embodiments, the piercing portion 422 has a square or rectangular cross-sectional shape (or outer profile). In some embodiments, the piercing portion 422 is a tapered shaped and/or has a tapered portion. In some embodiment the piercing portion 422 has a tapered portion along a specified portion that is configured to be disposed within a groove of a deflection member. The tapered portion more may be configured so that the piercing portion 422 may be more easily deflected within a deflection member.

As shown in FIG. 4A, piercing portion 422 has a straight shape. In other words, the piercing portion 422 is aligned along a line. Although not shown in FIG. 4A, in some embodiments, the piercing portion 422 has a curved portion configured to slidably move within a curve portion of a deflection member. In other words, the piercing portion 422 may have a curved portion with a predefined or fixed curvature. In other words, the piercing portion 422 can be constructed so that the piercing portion 422 is relaxed (or biased) in a curved shape. In some embodiments, the piercing portion 422 has a curvature that is the same as (or substantially the same as) a curvature of a deflection member.

In some embodiments, the piercing portion 422 has an end (not shown) that is configured to pierce a tissue of a body of a patient. Thus, the piercing portion 422 may have a sharp end or a blunt end (not shown). In some embodiments, the piercing portion 422 defines a dilating end configured to dilate a tissue of a patient.

The connector 426 can be any type of connector that can be used to couple the piercing portion 422 to the tether portion 424. In some embodiments, the connector 426 is a connector into which a portion of the tether portion 424 and/or the piercing portion 422 may be press fit. In some embodiments, the connector 426 is made of, for example, a metal, a polymer, and/or so forth. In this embodiment, the connector 426 is a crimp type connector. In some embodiments, the piercing portion 422 is coupled to the tether portion 424 without the use of a connector such as connector 426. A zoomed-in view (within area M) of the connector 426 is shown in FIG. 4B.

FIG. 4B is a zoomed-in view of the connector 426 of the elongate member 420 shown in FIG. 4A. As shown in FIG. 4B, the tether portion 424 is wrapped around a peg 428 disposed within the connector 426. Also as shown in FIG. 4B, the piercing portion 422 is inserted into a hole 427 defined by the connector 426, and the connector 426 is crimped around the piercing portion 422. In some embodiments, the connector 426 is constructed as a tube (e.g., a polymeric tube, a metal to) that may be crimped around the piercing portion 422 and/or the tether portion 424. In some embodiments, the piercing portion 422 may have a threaded portion that may be screwed into a threaded portion of the connector 426. In some embodiments, the piercing portion 422 and/or the tether portion 424 are coupled to the connector 426 using, for example, a pressfit, a screw, a rivet, glue (e.g., epoxy), and/or some other mechanical mechanism. In some embodiments, the piercing portion 422 and/or the tether portion 424 may be removably coupled to the connector 426.

In some embodiments, the tether portion 424 is made of a slender strand or fiber of a material or multiple materials. In some embodiments, the fiber is in the form of a filament, a leader, a thread, a rope, a strand, a suture, and/or so forth. In some embodiments, the fiber is braided or a mono filament, or can be of any cross-sectional shape such as a round shape, a square shape, a rectangular shape, an oval shape, and/or so forth. In some embodiments, at least a portion of the tether portion 424 is made of a biologic material, a bovine material, a cadaveric material, an absorbable material, and/or so forth. In some embodiments, at least a portion of the tether portion 424 is coated with a material. Although shown in FIG. 4A as a tether loop, in some embodiments, the tether portion 424 includes is a single strand that is configured to be secured to an implant (not shown) that is releasable, or not releasable.

In some embodiments, the connector 426 is a few millimeters (e.g., 2 mm, 4 mm) in length. In some embodiments, the connector 426 is less than a few millimeters in length or greater than a few millimeters in length.

Although not shown in FIG. 4A or 4B, in some embodiments, the connector 426 has a distal end 429 that defines a dilating end configured to dilate a tissue of a patient. In some embodiments, the dilating end of the connector 426 may be pushed through a tissue of a patient after the piercing portion 422 has been pushed through the tissue of the patient. Because the connector 426 may have a larger cross-sectional area (or outer profile) than a cross-sectional area (or an outer profile) of the piercing portion 422, the dilating end of the connector 426 may dilate the tissue of the patient so that the connector 422 may be pushed through the tissue of the patient in a desirable fashion.

In some embodiments, the connector 426 can be used to associate (e.g., couple) an implant (not shown) to an elongate member (not shown) after at least a portion of the piercing portion 422 of the elongate member has been disposed within a body of a patient via a deflection member (not shown). For example, in some embodiments, the tether portion 424, which is coupled to an implant, and connector 426 may be coupled to (e.g., crimped to) a proximal end of the piercing portion 422 after at least a medial portion of the piercing portion 422 has been deflected by a deflection member (not shown) into a body of a patient. A distal portion of the piercing portion 422 may be disposed outside of the body of the patient when the connector 426 (and tether portion 424) is coupled to the proximal end of the piercing portion 422. The distal portion of the piercing portion 422 may be pulled so that the connector 426 and at least a portion of the tether portion 424 coupled to the piercing portion 422 may be pulled outside of the body of the patient, and the implant, which is coupled to the tether portion 424, may be disposed at a desirable location (e.g., position) within the body of patient.

As another example, at least a medial portion of the piercing portion 422 may be deflected by a deflection member (not shown) and disposed within a body of a patient. In this embodiment, the connector 426 is coupled to a proximal end of the piercing portion 422 as the piercing portion 422 is being disposed within the body of the patient. The tether portion 424, which is coupled to an implant, may be coupled to the connector 426 of the piercing portion 422 so that the tether portion 424 (and implant) may be associated with the piercing portion 422 that already has a portion disposed within the body of patient. A distal portion of the piercing portion 422 may be disposed outside of the body of the patient when the tether portion 424 is coupled to the connector 426 of the piercing portion 422. The distal portion of the piercing portion 422 may be pulled so that the connector 426 and at least a portion of the tether portion 424 coupled to the piercing portion 422 may be pulled outside of the body of the patient, and the implant, which is coupled to the tether portion 424, may be disposed a desirable location within the body of patient.

Although not shown in FIG. 4A or FIG. 4B, in some embodiments, the elongate member 420 may have a piercing portion 422 that is configured to be coupled directly to an implant. In such embodiments, the piercing portion 422 may not be configured to be coupled to the tether portion 424 via the connector 426. For example, the piercing portion 422 may be directly fused to the tether portion 424, or the tether portion 424 may be an extension of the piercing portion 422 (so that the tether portion 424 is made from the same material as the piercing portion 422). Also, although not shown, in some embodiments, an elongate member may have a piercing portion that is configured to be directly coupled to an implant without a tether portion. In such embodiments, the piercing portion may define a connector configured to be coupled to directly to the implant. In some embodiments, the piercing portion may be directly coupled to an implant, or the implant may be an extension of the piercing portion.

FIG. 5 is a diagram that illustrates an injection needle 560 configured to inject a fluid into a passageway associated with an elongate member 520, according to an embodiment. As shown in FIG. 5, a piercing portion 522 of the elongate member 520 has a distal portion 524 disposed outside of a portion 72 of a body of a patient (as represented with a solid line) and a proximal portion 526 disposed within the portion 72 of the body of the patient (as represented with a dashed line). The elongate member 520 can be similar to the elongate members described herein and can be inserted into the portion 72 of the body of the patient using one or more deflection members similar to those described herein. The distal portion 524 of the piercing portion 522 of the elongate member 520 may be pushed from a position within the portion 72 of the body of the patient to a position outside of the portion 72 of the body of the patient in direction O.

In this embodiment, the injection needle 560 defines a lumen (not shown) configured to be disposed over the piercing portion 522. In this embodiment, injection needle 560 is moved over the piercing portion 520 along direction N, which is opposite direction O. In some embodiments, the injection needle 560 is moved along the piercing portion 522 into the body of the patient (along a passageway defined at least in part by the piercing portion 522). In some embodiments, for example, a lumen defined by the needle member 560 may be used to deliver medication or anesthesia to the body of the patient during a procedure to place an implant (not shown) coupled to the elongate member 520 within the body of the patient. In some embodiments, the injection needle 560 may be used to help hydro-dissect the bodily tissue during an implantation procedure. In some embodiments, a fluid (e.g., a local anesthetic) is injected into the body of the patient after the injection needle 560 is placed within a desirable location (e.g., a midline incision) in the body of the patient along the piercing portion 522. In some embodiments, a fluid is injected into the body of the patient as the injection needle 560 is being moved along the piercing portion 522 of the elongate member 520.

The lumen defined by the injection needle 560 may be of any shape or size. For example, the cross-sectional shape of the lumen may be circular, square, or rectangular. In some embodiments, the injection needle 560 is made of a metal material, a polymer, a flexible material, and/or so forth.

Although not shown in FIG. 5, in some embodiments, the injection needle 560 is coupled to a syringe (e.g., coupled to a syringe via a tube). The syringe is configured to deliver a fluid to and/or draw a fluid from the injection needle 560. In some embodiments, the syringe is a 20 cc syringe. In other embodiments, the syringe is larger or smaller than 20 cc.

Figure 6A:
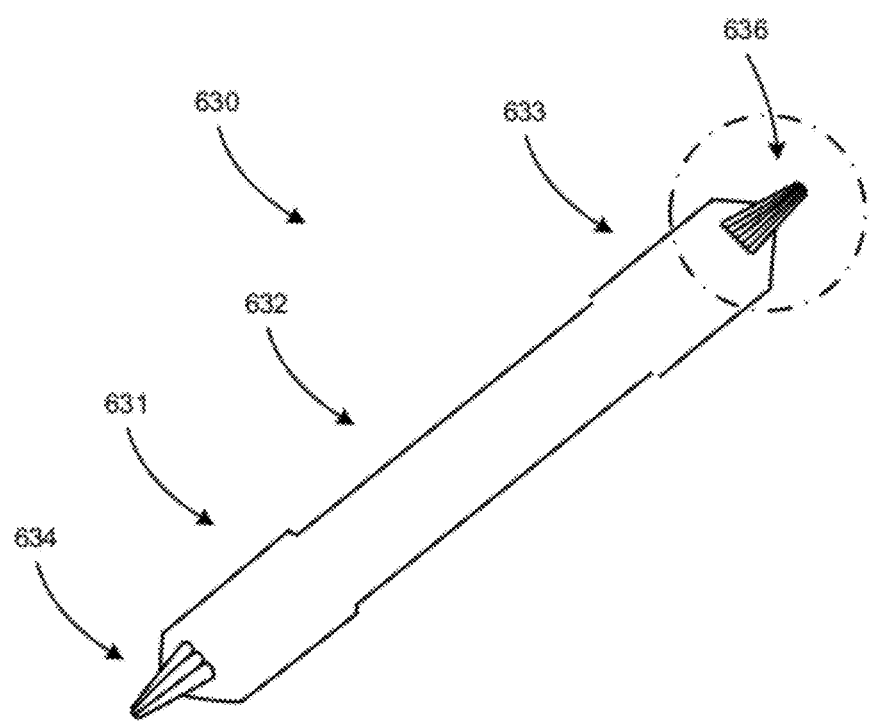
FIG. 6A is a top view of implant that may be implanted into a pelvic region of a patient.

The medical devices described herein (e.g., the deflection members and elongate members described herein) may be used to insert an implant into, for example, a pelvic region of a patient. For example, an implant 630 as illustrated in FIG. 6A may be implanted into a pelvic region of a patient using the medical devices. The implant 630 shown in FIG. 6A is a sling and includes a support portion 632, and connectors 634 and 636. Although not shown in FIG. 6A, each of the connectors 634 and 636 can be coupled to a tether portion such as the tether portion 424 of the elongate member 420 shown in FIGS. 4A and 4B.

The support portion 632 can be configured to be placed proximate a portion of the body of the patient and can be configured to provide support to the portion of the body. The connectors 634 and 636 can be configured to associate the implant 630 to the medical devices described herein (e.g., tether portions of an elongate member) during an implantation procedure.

In some embodiments, the implant 630 may be formed of any biocompatible material. In some embodiments, the implant 630 is formed of a mesh material. For example, the implant 630 may be formed of Advantage® mesh or the Polyform™ synthetic mesh, both as produced and/or sold by Boston Scientific Corporation. In some embodiments, the implant 630 is also made of a biologic material, a bovine material, a cadaveric material, an absorbable material, and/or so forth. In some embodiments, the implant 630 is formed of a polymer material. In some embodiments, the material of the implant 630 allows for tissue in-growth to secure the implant 630 to the bodily tissue of the patient.

As shown in FIG. 6A, in some embodiments, the implant 630 includes tangs 631 and 633 to help retain the implant 630 in place within the body of the patient. In such embodiments, the tangs 631 and 633 are configured to engage the bodily tissue surrounding the implant 630 help retain the implant 630 in place within the body of the patient. The terms "tanged" or "tangs" as used herein mean roughened or jagged edges or areas, such as can result from cutting a woven or knit mesh material.

Figure 6B:
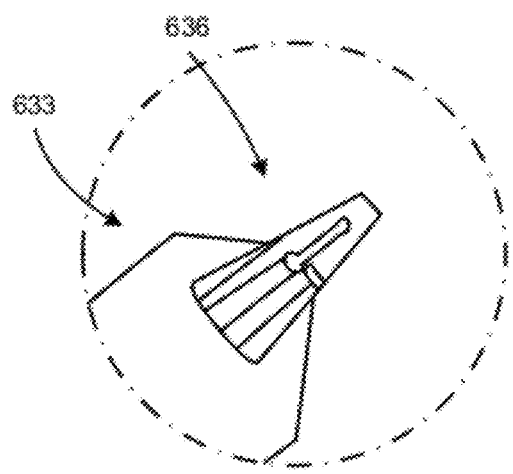
FIG. 6B is a zoomed-in view of the connector shown in FIG. 6A.

FIG. 6B is a diagram that illustrates a zoomed-in view of the connector 636 shown in FIG. 6A. As shown in FIG. 6B, the connector 636 has an L slot to which a tether portion (such as the tether portion 424 shown in FIG. 4A) may be coupled. In such embodiments, one end of the tether portion (which may or may not already be coupled to a piercing portion of an elongate member) may be inserted through the opening of loop connector 636, then threaded through at least a portion of the implant 630, and back out through the opening of the connector 636. In some embodiments, the connector 636 may be made of any type of material such as a polymer (e.g., polypropylene). In some embodiments, at least a portion of the connector 636 can be coupled to the implant using a heat stake, gluing, insert molding, swaging, and/or so forth.

In some embodiments, the connector 636 has a dilating distal end configured to dilate tissue of a patient. In some embodiments, the connector 636 may be moved from a position inside of a body of a patient to a position outside of a body of a patient during a procedure used to implant the implant 630 into the body of the patient. In such embodiments, the dilating distal end of the connector 636 may facilitate movement of tissue as the connector 636 is pushed against the tissue so that the connector 636 may be moved from the position inside of the body of the patient to the position outside of the body of the patient.

Referring back to FIG. 6A, when implanting the implant 630 into a body of a patient using an inside-out procedure, a tether portion of an elongate member (not shown) may be coupled to or otherwise associated with the implant 630. In some embodiments, the tether portion of the elongate member may be coupled to the connectors 634 and/or 636 of the implant 630. A deflection member (not shown), such as the deflection members described herein, may be inserted into, for example, a midline incision within a vagina of the patient. A piercing portion (not shown) of the elongate member may be deflected along (e.g., along a groove of) the deflection member until a distal end of the piercing portion moves through the body of the patient and then outside of the body of the patient. The distal end of the piercing portion may then be pulled until the connector 636 of the implant 630 is disposed outside of the body of the patient (through skin of the body of the patient). In some embodiments, a portion (e.g., a distal portion) of the elongate member and/or a portion of the implant that is disposed outside of the body of the patient may be used to adjust a location of the implant 630 within the body of the patient. After the implant 630 has been disposed in a desirable location within the body of the patient, a portion of the tanged portion 633 of the implant 630 that is disposed outside of the body of patient may be cut and a portion of the tanged portion 633 of the implant 630 that remains inside of the body of the patient can function as an anchor for the implant 630. After the implant 630 has been placed within the body of the patient, the midline incision is sutured closed. In some embodiments, the implant 630 may be associated with the elongate member after the piercing portion of the elongate member has been deflected along the deflection member.

In some embodiments, at least a portion of a tether portion associated with (e.g., coupled to) the connector 636 of the implant 630 is configured to remain within the body of the patient and/or to function as an anchor for the implant 630 within the body of the patient. In such embodiments, at least a portion of the tether portion associated with (e.g., coupled to) the connector 636 of the implant 630 may be moved outside of the body of the patient. The portion of the tether portion outside of the body of the patient can be cut, and a portion of the tether portion inside of the body of patient may remain inside of the body of patient. As a specific example, in some embodiments, when one or more tether portions associated with the implant 630 are placed within a body of the patient, the implant 630 is positioned, adjusted, and/or tensioned (the implant 630 may have a center loop for loosening (not shown)). One or more of the tether portions associated with the implant 630 may be removed by cutting one side of a tether portion (e.g., tether loop) and pulling the cut loop away from the body of the patient to remove the loop and/or a portion of the loop can be left behind by cutting just above skin level and tucking the remainder of the tether portion underneath the skin or the entire tether portion or portion of the tether portion can remain external to the body for subsequent adjustment if needed within, for example, a few days. In some embodiments, the tether portion is taped or "spooled" to the skin surface of the patient.

In some embodiments, the connector 636 is not moved (e.g., pulled) to a position outside of the body of the patient. Instead, the connector 636 is configured to remain within the body of the patient and/or to function as an anchor for the implant 630 within the body of the patient.

In some embodiments, after at least a portion of the implant 630, and/or a portion of the elongate member associated with the implant 630 is inserted into a body of a patient (e.g., pulled through the skin of the patient), the deflection member may be removed from the body of the patient. In some embodiments, after at least a portion of the implant 630 is disposed within the body of the patient, at least a portion of a piercing portion of an elongate member that is disposed outside of a body of the patient may be cut off or removed from (e.g., decoupled from) a tether portion of the elongate member.

Figure 7:
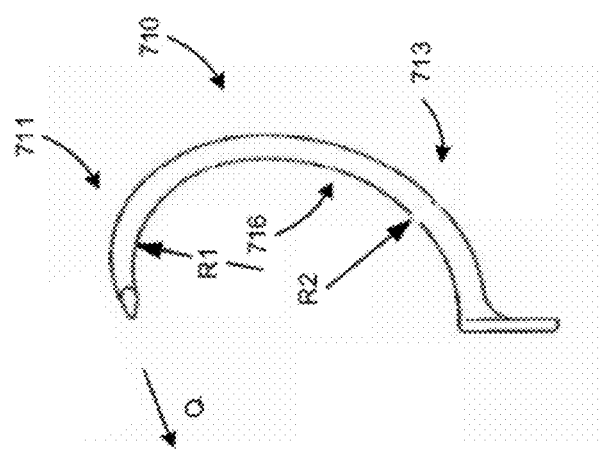
FIG. 7 is a side view of a deflection member, according to an embodiment.

FIG. 7 illustrates a deflection member 710, according to an embodiment. In some embodiments, the deflection member 710 is used to insert an implant into a body of the patient via an obturator of the patient. The deflection member 710 shown in FIG. 7 has two different radii of curvature associated with two different portions of the deflection member 710. Specifically, the deflection member 710 defines a radius R1 of curvature for a first portion 711 of the deflection member 710 and defines a radius R2 of curvature for a second portion 713 of the deflection member 710. The curvature of the first portion 711 and the curvature of the second portion 713 are defined so that an elongate member (not shown) deflected within a grooved channel 716 of the deflection member 710 may be directed (along direction Q) close to, for example, the ischio pubic ramus and away from lateral nerves of a patient. In some embodiments, the deflection member 710 may have variable radii of curvature (more than that shown in FIG. 7).

In some embodiments, the radius R2 of curvature is 50% larger than the radius R1 of curvature. In some embodiments, the radius R2 of curvature is more than 50% larger than the radius R1 of curvature. In some embodiments, the radius R2 of curvature is less than 50% larger than the radius R1 of curvature. In some embodiments, the radius R2 of curvature is smaller than the radius R1 of curvature.

In some embodiments, the radius R1 of curvature and the radius R2 of curvature can approximately define a single radius of curvature of 3 cm. In some embodiments, the combined radius R1 of curvature and radius of curvature R2 can be greater than 3 cm (e.g., 3.3 cm, 5 cm, 10 cm), or can be less than 3 cm (e.g., 2.5 cm, 1 cm).

In some embodiments, a straight portion can be disposed between the curved portions associated with radius R1 of curvature and radius R2 of curvature. In some embodiments, the straight portion can have a length of approximately 1 cm. In some embodiments, the straight portion can have a length greater than 1 cm (e.g., 2 cm, 3 cm, 5 cm, 10 cm), or can have a length less than 1 cm (e.g., 0.5 cm, 0.2 cm).

In some embodiments, the deflection member 710 is made of multiple types of materials (e.g., polymeric materials, metallic materials). In some embodiments, the first portion 711 of the deflection member may be made of a first material that is welded to a second material used to make the second portion 713 of the deflection member 710.

Figure 8:
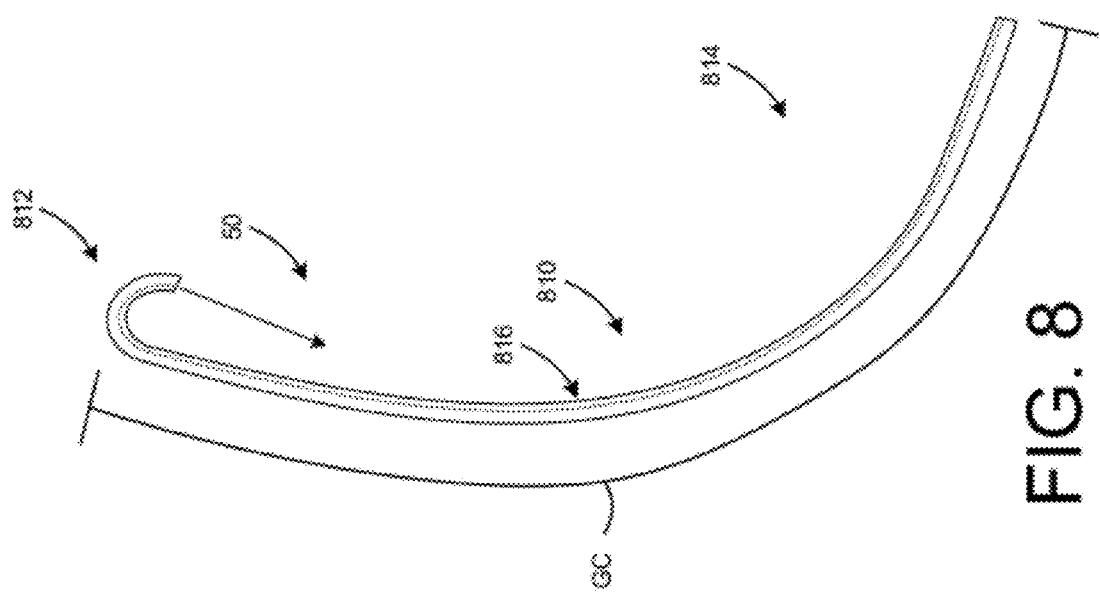
FIG. 8 is a side view of another deflection member, according to an embodiment.

FIG. 8 illustrates another deflection member 810, according to an embodiment. As shown in FIG. 8, the deflection member 810 has a distal end 812 with a relatively tight curvature (short radius of curvature), and a proximal end 814 with a relatively loose curvature (long radius of curvature). In some embodiments, the deflection member 810 may be used as an insertion guide for a single incision type of approach for inserting an implant into a body of a patient. Specifically, an elongate member (e.g., a piercing portion elongate member) that is deflected by the deflection member 810 may exit the same incision into which the deflection member 810 (and the elongate member) is originally inserted. Thus, only a single incision may be needed to perform an implant procedure. In some embodiments, the deflection member 810 shown in FIG. 8 can be configured for placement of an implant (such as the implant 130 shown in FIG. 1 and/or the implant 630 shown in FIG. 6A) through a Cooper's ligament of a patient, or a portion (e.g., a leg) of a pelvic floor implant through a Sacrospinous ligament and/or Arcus tendineus of a patient.

In some embodiments, a radius of curvature of the distal end 812 is approximately 1 cm. In some embodiments, the radius of curvature of the distal end 812 is greater than 1 cm or less than 1 cm. In some embodiments, a length GC of the deflection member 810 can be between approximately 15 to 25 cm long. In some embodiments, the length GC of the deflection member can be less than 15 cm (e.g., 10 cm, 5 cm), or can be greater than 25 cm (e.g., 30 cm, 35 cm).

In some embodiments, an elongate member (not shown) is moved within a groove 816 of the deflection member 810, through tissue (including ligament) and back out through the same incision along the same groove 816. In some embodiments, the deflection member 810 is used to place an implant (not shown) using a Cooper's ligament or tissue along the path towards the obturator by suturing a tether portion associated with the implant through tissue and back out of the same incision. In some embodiments, the deflection member 810 is used to place an implant through the sacrospinous ligament, the arcus tendineus, and/or other pelvic locations of the patient.

In some embodiments, a distal end 812 of the deflection member 810 may have a distal end configured to pierce and/or dilate a tissue of a patient. In some embodiments, a proximal end 814 of the deflection member 810 may have a tab (e.g., a tab portion) that can be used to insert and/or remove the deflection member 810 from the body of a patient. In some embodiments, the proximal end 814 of the deflection member 810 may be grasped (with or without a tab) using a hemostat.

Figure 9:
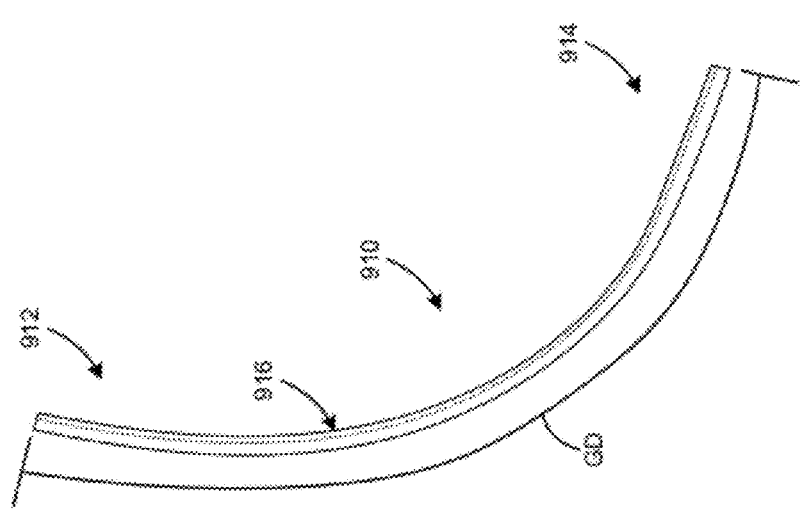
FIG. 9 is a side view of another deflection member, according to an embodiment.

FIG. 9 is a diagram that illustrates yet another deflection member 910, according to an embodiment. The deflection member 910, like the other deflection members described herein, includes a groove 916 within which at least a portion of an elongate member (not shown) can be slidably moved. In some embodiments, the deflection member 910 shown in FIG. 9 is used to insert an implant into a patient using a retro-pubic (bottom-up) approach and/or a super-pubic (top-down) approach.

In some embodiments, a distal end 912 of the deflection member 910 may have a distal end configured to pierce and/or dilate a tissue of a patient. In some embodiments, a proximal end 914 of the deflection member 910 may have a tab that can be used to insert and/or remove the deflection member 910 from the body of a patient. In some embodiments, the proximal end 914 of the deflection member 910 may be grasped (with or without a tab) using a hemostat. In some embodiments, a length GD of the deflection member 810 can be between approximately 20 to 25 cm long. In some embodiments, the length GD of the deflection member can be less than 20 cm (e.g., 15 cm, 10 cm, 5 cm), or can be greater than 25 cm (e.g., 30 cm, 35 cm).

Figure 10A:
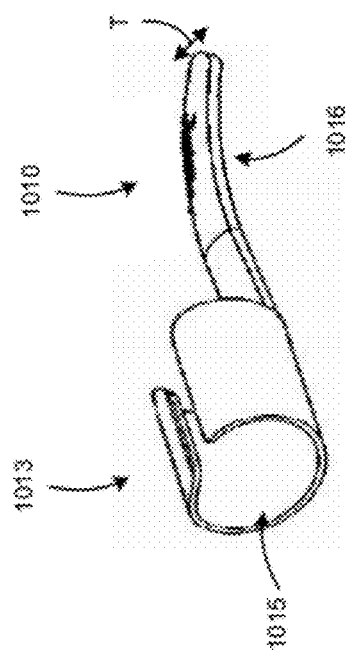
FIG. 10A illustrates a deflection member that has a clip.

FIG. 10A is a diagram that illustrates a deflection member 1010 that has a clip 1013. In some embodiments, the clip 1013 can be referred to as a C clip. The clip 1013 can be used by, for example, a physician to insert and/or remove the deflection member 1010 from a body of the patient. Specifically, a finger of the physician can be inserted into tube-shaped region 1015 defined by the clip 1013. In some embodiments, the region 1015 can be referred to as a finger fit region. The deflection member 1010 defines a groove 1016 configured to deflect an elongate member one the elongate member is slidably moved within the groove 1016.

Figure 10B:
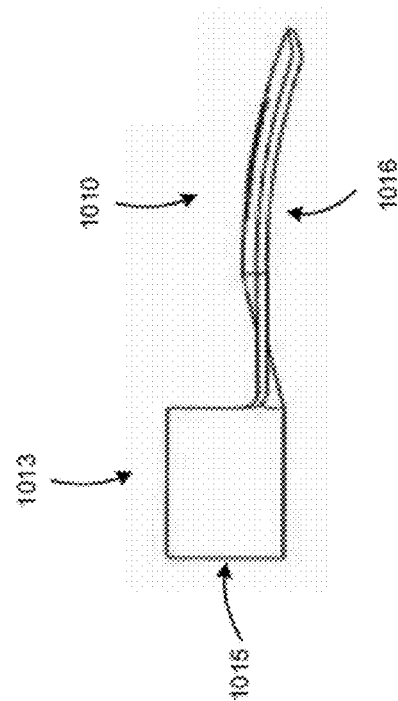
FIG. 10B is a side view of the deflection member shown in FIG. 10A.

FIG. 10B is a diagram that illustrates a side view of the deflection member 1010 shown in FIG. 10A. As shown in FIG. 10B, the groove 1016 of the deflection member 1010 has a relatively long radius of curvature compared with the radius of curvature of, for example, the deflection member 110 shown in FIG. 1A, the deflection member 210 shown in FIG. 2, the deflection member 310 shown in FIGS. 3A through 3D, and so forth.

In some embodiments, the clip 1013 can be coupled to any of the deflection members described herein. For example, the clip 1013 can be coupled to the deflection member 310 shown in FIG. 3A. In such embodiments, the clip 1013 can be coupled to the deflection member 310 instead of the tab 313 shown in FIG. 3A.

In some embodiments, the deflection member 1010 has a width T that is approximately the same as a width of an implant (such as the implant 630 shown in FIG. 6A). In some embodiments, the width T of the deflection member 1010 is less than a centimeter (e.g., approximately 0.2 centimeters). In some embodiments, the width T of the deflection member 1010 is greater than a centimeter. In some embodiments, the deflection member 1010 has a width T that is less than that of an implant, or greater than that of an implant.

In some embodiments, the deflection member 1010 shown in FIGS. 10A and 10B is configured to be used in conjunction with at least one of the other deflection members described herein. For example, the deflection member 910 shown in FIG. 9 can be inserted into a body of a patient using an outside-in approach. An elongate member (such as elongate member 120 shown in FIG. 1A) can be deflected against the deflection member 910 until at least a portion of the elongate member is disposed within a body of a patient. The elongate member may be associated with an implant (such as implant 630 shown in FIG. 6A). The deflection member 1010 can be inserted into an anterior vaginal incision to meet the portion of the elongate member that is disposed within the body of the patient. The elongate member can be pushed so that the portion of the elongate member is deflected against the deflection member 1010 (e.g., against the groove 1016 of the deflection member) and out of the anterior vaginal incision of the patient. Thus, the deflection member 1010 can be used to deflect at least a portion of the elongate member out of the body of the patient. The other deflection members (such as deflection member 310 shown in FIG. 3A) described herein can be used in a similar fashion to that described above in connection with the deflection member 1010.

Figure 11B:
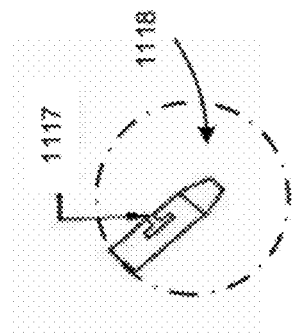
FIG. 11B is a zoomed-in view of the T slot shown in FIG. 11A.
Figure 11A:
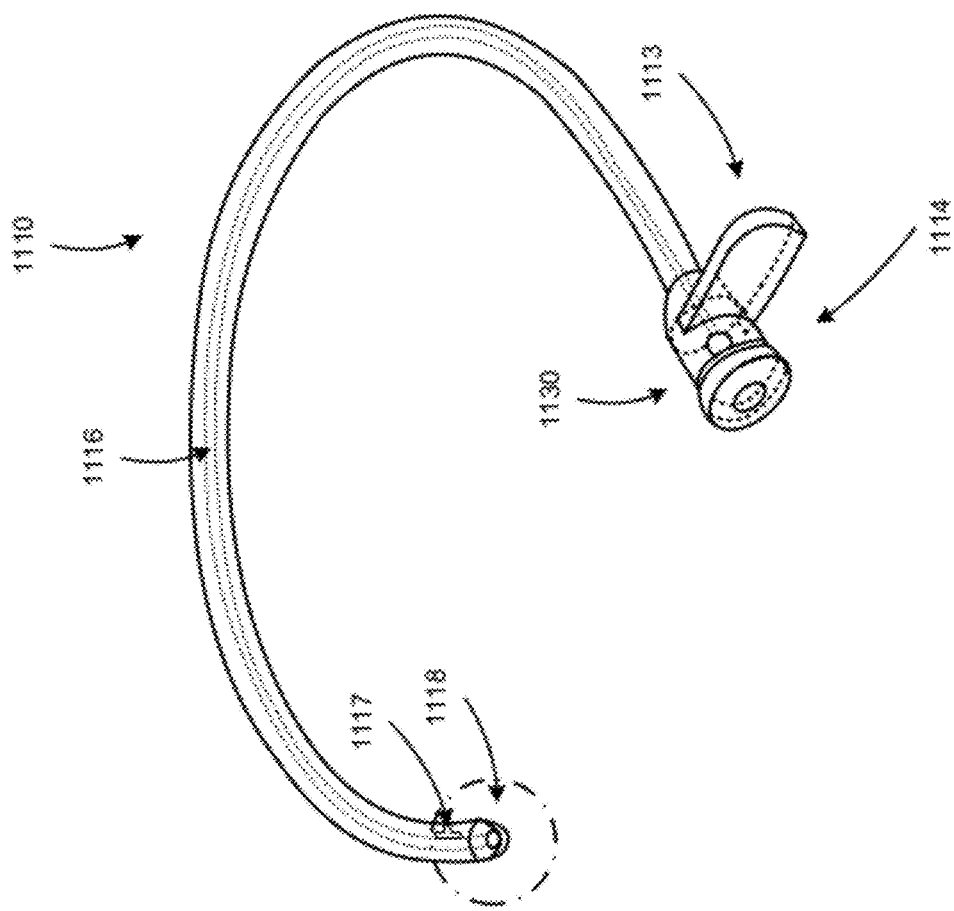
FIG. 11A is a perspective view of a deflection member that defines a lumen.

FIG. 11A is a schematic diagram that illustrates a deflection member 1110 that defines a lumen 1116. In some embodiments, the deflection member 1110 is configured to pass from an entry point of a body of a patient to an exit point of the body of the patient. Thus, in some embodiments, the deflection member 1110 has a length sufficient to span between two incisions within the body of the patient. In some embodiments, the deflection member 1110 is inserted into a single incision within the body of the patient and does not extend between two different incisions within the body of the patient.

In some embodiments, the lumen 1116 is constructed from a tube. In some embodiments, the tube has a 16 gauge outer diameter. In some embodiments, the tube has an outer diameter that is greater than 16 gauge or less than 16 gauge. In some embodiments, the lumen 1116 has an inner diameter that is several hundreds of a centimeter (e.g., 0.05 cm, 0.02 cm). In some embodiments, the lumen 1116 is defined so that a fluid (e.g., an anesthetic and aspirate) may be conveyed via the lumen 1116. In some embodiments, the lumen 1116 defined by the deflection member 1110 may be of any shape or size. For example, the cross-sectional shape (or outer profile) of the lumen may be circular, square, or rectangular.

As shown in FIG. 11A, at a proximal end 1114 of the deflection member 1110 has a medical luer configured to be coupled to, for example, a syringe. Also, at the proximal end 1114 of the deflection member 1110 has a tab 1113 that may be grasped during a medical procedure. For example, the tab 1113 may be coupled to a hemostat that can be used to direct the deflection member 1110 as the deflection member 1110 is inserted into and/or removed from the body of a patient.

In this embodiment, the deflection member 1110 defines a T slot 1117 in a distal end 1118 of the deflection member 1110. A zoomed in view of the T slot 1117 is shown in FIG. 11B. The T slot 1117 is configured so that a tether portion (such as the tether portion 424 shown in FIG. 4A with or without an elongate member) may be coupled to the distal end 1118 of the deflection member 1110.

In some embodiments, the deflection member 1110 can be passed from a position inside of a body of the patient to a position outside a body of the patient via a first incision using an obturator approach. A tether (e.g., a tether loop, a tether portion) without an elongate member can be attached to the distal end 1118 and pulled back through the first incision, removing the deflection member 1110. An implant of (e.g., the implant shown in FIG. 6A) can be attached to the tether to be pulled back to a position outside a body of the patient via the first incision using an obturator approach. These steps can be repeated on the contra lateral side to place the other side of the implant within the body of the patient.

In some embodiments, the deflection member 1110 is passed from a position outside of a body of the patient to a position inside a body of the patient via a first incision using an obturator approach. The deflection member 1110 may be pushed until the distal end 1118 of the deflection member 1110 exits through a second incision in the body of the patient. An elongate member (not shown) may be deflected within the lumen 1116 defined by the deflection member 1110. In such embodiments, the elongate member can be defined by a piercing portion, or by a piercing portion and tether portion. In some embodiments, the elongate member is moved into the distal and 1118 of the deflection member 1110 or into a proximal end 1114 of the deflection member 1110. After the elongate member has been placed within the body of the patient via the deflection member 1110, the deflection member 1110 may be removed through the first incision, leaving the elongate member disposed within the body of the patient. An implant may be associated with a proximal end or distal end of the elongate member (e.g., a tether portion of the elongate member may be attached to the implant), and the elongate member can be withdrawn (e.g., moved out, pulled out) from the body of the patient via the first or second incision (depending on the end to which the implant is associated) so that the implant is moved into (e.g., pulled into) the body of the patient.

As another example, after the deflection member 1110 is disposed within a body of the patient via an outside incision using an outside-in obturator approach, a tether portion of an implant (not shown) (with or without a piercing portion) may be attached to the T slot 1117 at an incision of a patient midline for placement of the implant. As the deflection member 1117 is withdrawn from the body of the patient, the implant, which is attached to the deflection member 1110, may be placed within the body of the patient.

Figure 11C:
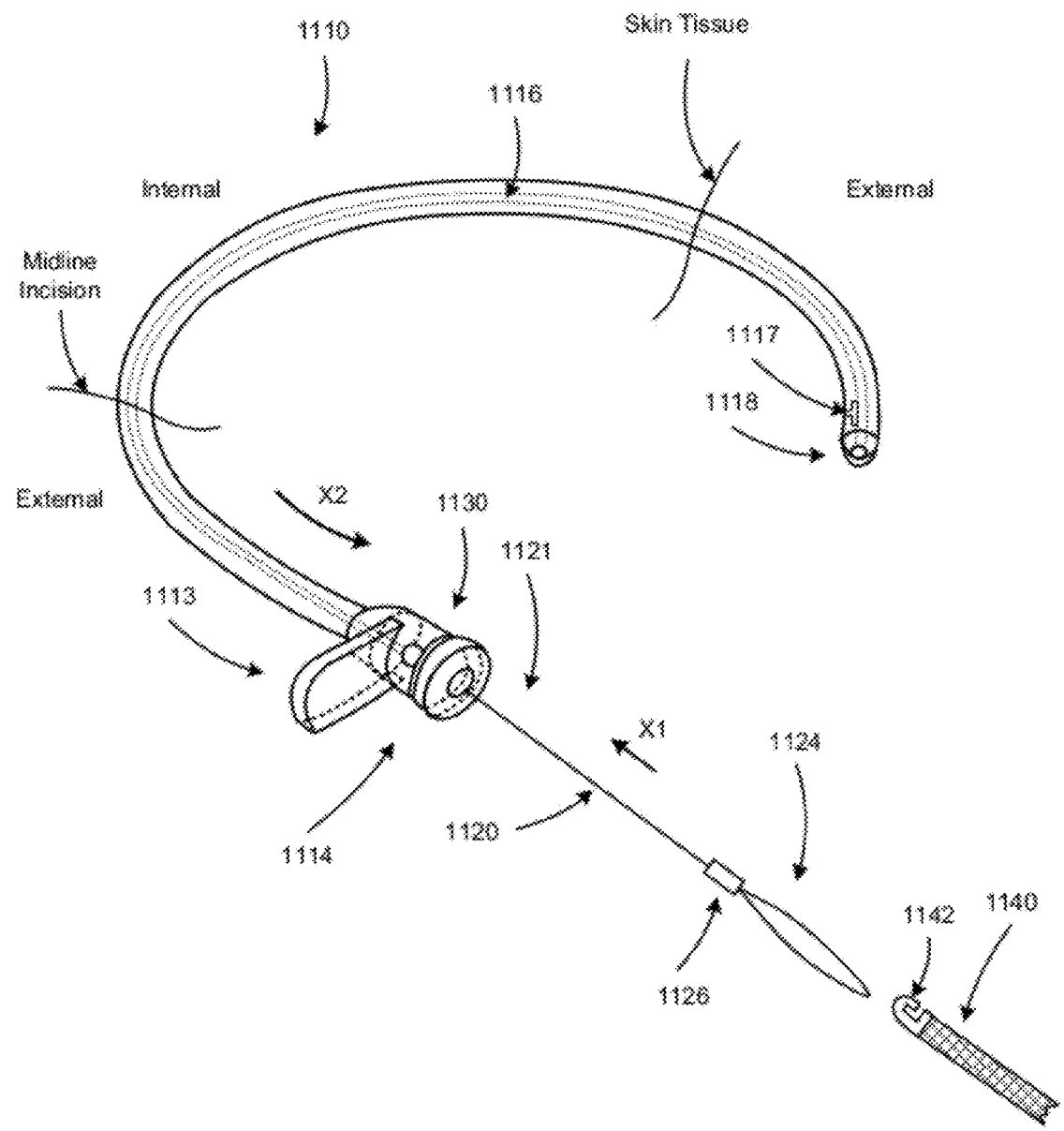
FIGS. 11C through 11F are diagrams that illustrate methods of using the deflection member shown in FIG. 11A.

FIGS. 11C through 11F are diagrams that illustrate methods of using the deflection member 1110 shown in FIG. 11A. As shown in FIG. 11C, the deflection member 1110 may be inserted into a body of a patient through a midline incision and then through a skin tissue using an inside-out approach until the distal end 1118 of the elongate member 1110 exits the skin tissue of the patient. An elongate member 1120, which has a tether 1124 (e.g., tether loop) and a connector 1126, can be inserted (e.g., slidably inserted) into the lumen 1116 of the deflection member 1110 along direction X1. In some embodiments, the elongate member 1120 may be slidably moved within the lumen 1116 until at least a portion of the distal portion 1121 of the elongate member 1120 extends out of the proximal end 1114 of the deflection member 1110. After at least a portion of the elongate member 1120 is disposed within the lumen 1116, the deflection member 1110 may be removed from the body of the patient over (e.g., slidably over) the elongate member 1120 along direction X2 (opposite the direction of insertion of the deflection member 1110) such that at least a portion of the elongate member 1120 remains within the body of the patient and a distal portion 1121 of the elongate member 1120 extends from the skin tissue of the patient. The elongate member 1120 may be coupled to an implant 1140 via an L-connector 1142 (or a different type of connector), and the distal portion 1121 of the elongate member 1120 extending from the skin tissue of the patient may be pulled so that the implant 1140 may be moved into the body of the patient. In some embodiments, the elongate member 1120 may be pulled until at least a portion of the tether 1424 and/or at least a portion of the implant 1140 passes through the midline incision (to an internal side of the midline incision).

Figure 11D:
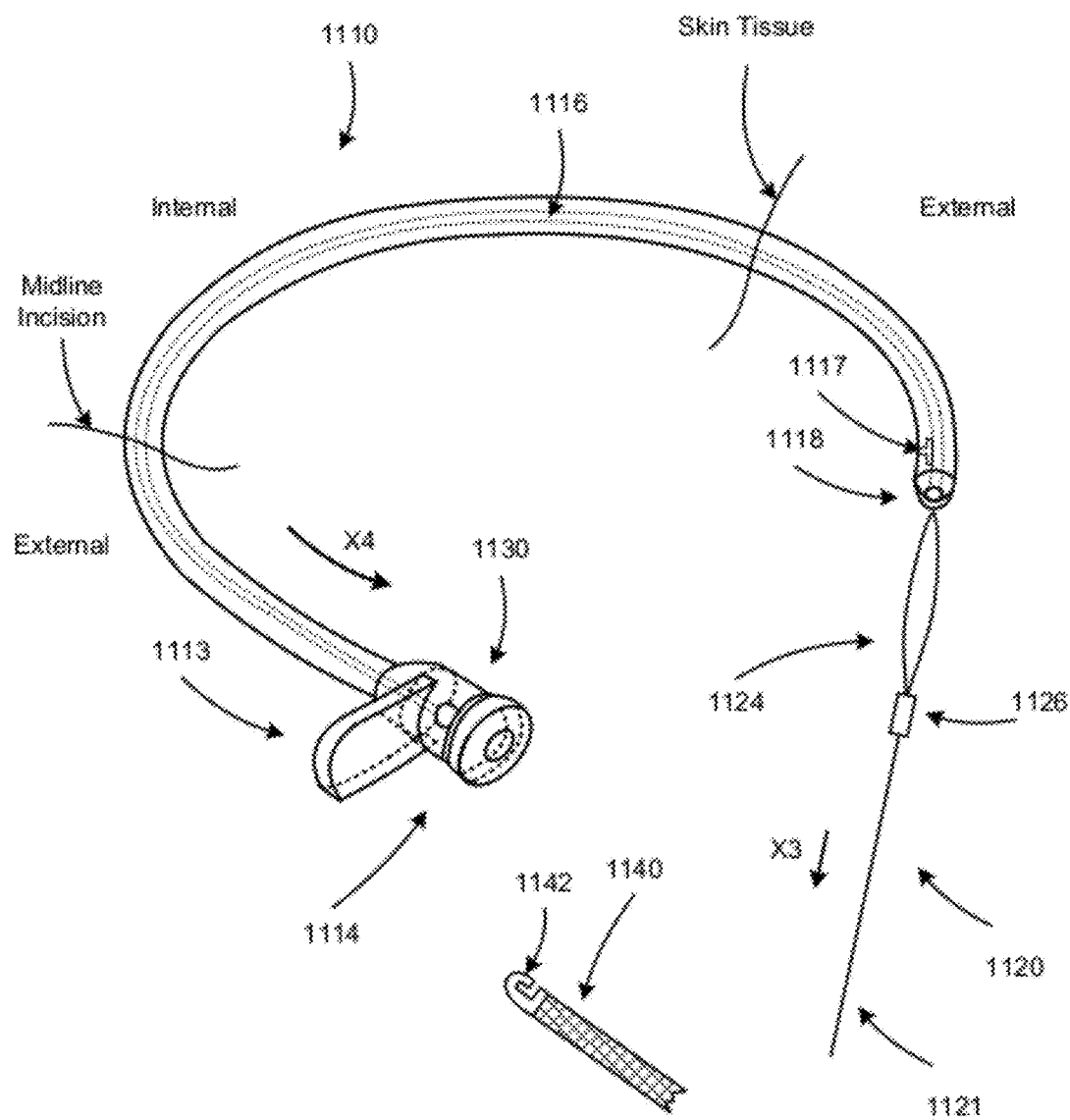

In the embodiment shown in FIG. 11D, the deflection member 1110 may be inserted into the body of the patient through the midline incision and then through the skin tissue using an inside-out approach until the distal end 1118 of the elongate member 1110 exits the skin tissue of the patient. The tether 1124 of the elongate member 1120 may be coupled to the T-slot 1117 (or another type of slot) of the deflection member 1110, and the deflection member may be pulled along direction X4 (opposite the direction of insertion of the deflection member 1110) so that the tether 1124, the connector 1126, and/or the elongate member 1120 may be moved into the body of the patient (via the skin tissue). The deflection member 1110 may be pulled along direction X4 until at least a portion of the tether 1124 (or another portion of the elongate member 1120) exits the midline incision and is disposed on the external side of the midline incision. Accordingly, the deflection member 1110 may be removed from the body of the patient. At least a portion of the elongate member 1120 can remain within the body of the patient and the distal portion 1121 of the elongate member 1120 can extend from the skin tissue of the patient (on the external side). The tether 1124 (i.e., the portion of the tether 1124 disposed on the external side of the midline incision) may be coupled to the implant 1140 via the L-connector 1142 (or a different type of connector), and the distal portion 1121 of the elongate member 1120 extending from the skin tissue of the patient may be pulled (away from the skin tissue of the patient) so that the implant 1140 may be moved into the body of the patient. In some embodiments, the elongate member 1120 may be pulled until at least a portion of the implant 1140 passes through the midline incision (to an internal side of the midline incision).

Figure 11E:
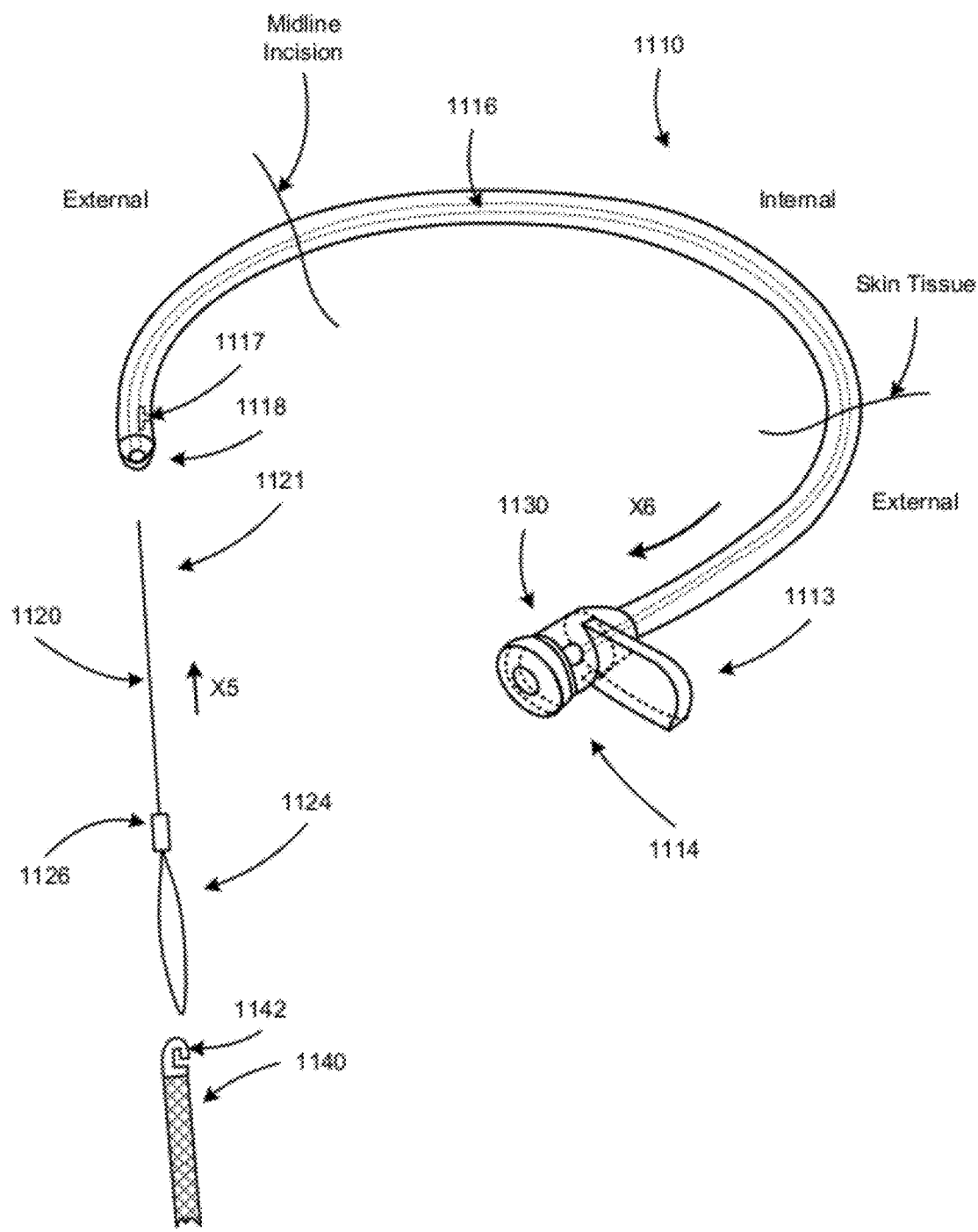

As shown in FIG. 11E, the deflection member 1110 may be inserted into a body of a patient through a skin incision and then through a midline incision using an outside-in approach until the distal end 1118 of the elongate member 1110 exits the midline incision of the patient. The elongate member 1120, which includes the tether 1124 and the connector 1126, can be inserted (e.g., slidably inserted) into the lumen 1116 of the deflection member 1110 along direction X5 (opposite the direction of insertion of the deflection member 1110). In some embodiments, the elongate member 1120 may be slidably moved within the lumen 1116 until at least a portion of the distal portion 1121 of the elongate member 1120 extends out of the proximal end 1114 of the deflection member 1110.

After at least a portion of the elongate member 1120 is disposed within the lumen 1116, the deflection member 1110 may be removed from the body of the patient over (e.g., slidably over) the elongate member 1120 along direction X6 (away from the skin tissue) such that at least a portion of the elongate member 1120 remains within the body of the patient and a distal portion 1121 of the elongate member 1120 extends from the skin tissue of the patient.

In this embodiment, the elongate member 1120 may be coupled to the implant 1140 via the L-connector 1142 (or a different type of connector) before or after the deflection member 1110 is removed from the body of the patient. The distal portion 1121 of the elongate member 1120 extending from the skin tissue of the patient may be pulled (away from the skin tissue of the patient) so that the implant 1140 may be moved into the body of the patient. In some embodiments, the elongate member 1120 may be pulled until at least a portion of the tether 1424 and/or at least a portion of the implant 1140 passes through the midline incision (to an internal side of the midline incision).

Figure 11F:
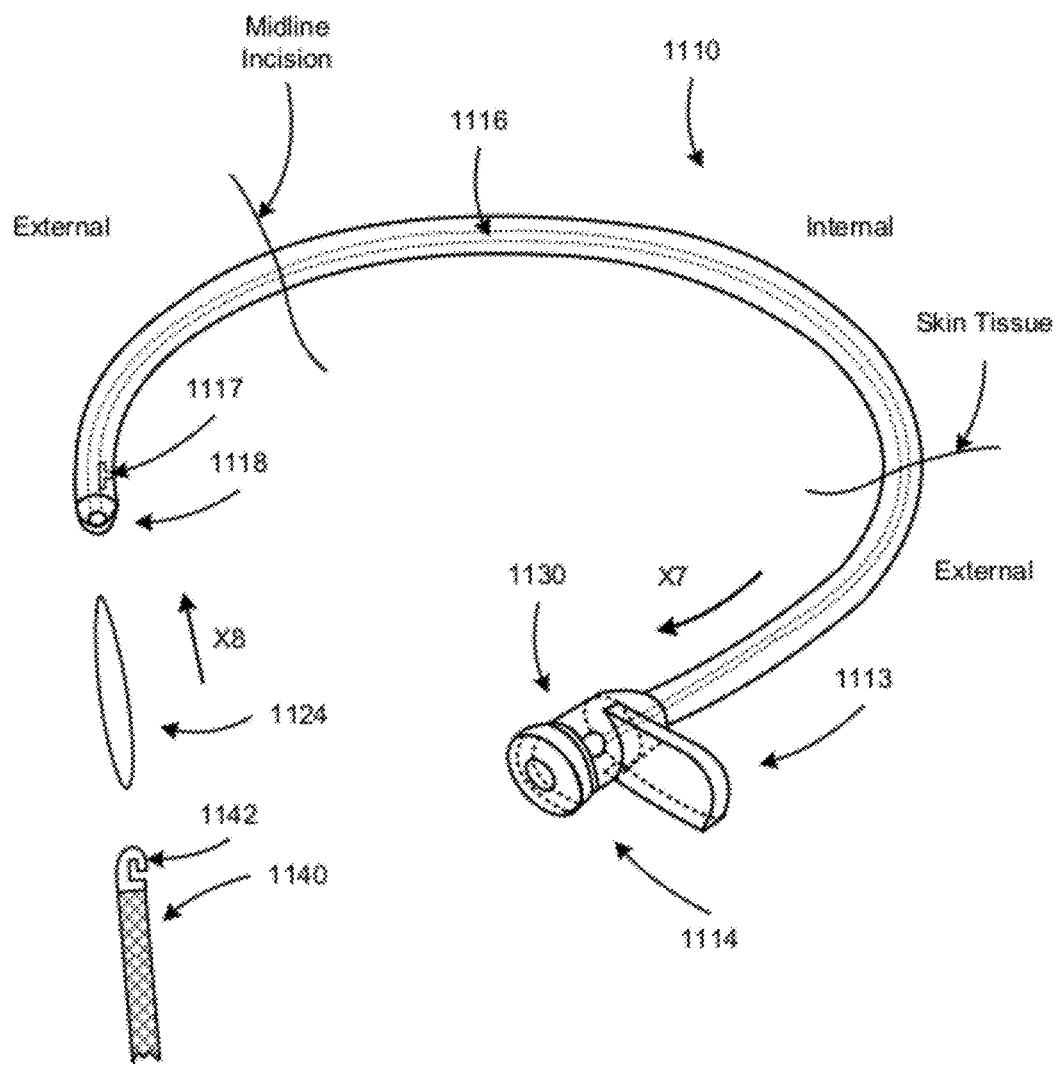

In the embodiment shown in FIG. 11F, the deflection member 1110 may be inserted into the body of the patient through the skin tissue and then through the midline incision using an outside-in approach until the distal end 1118 of the elongate member 1110 exits the midline incision of the patient. The tether 1124 (which is not coupled to an elongate member) may be coupled to the T-slot 1117 of the deflection member 1110, and the deflection member may be pulled along direction X7 (opposite the direction of insertion of the deflection member 1110) so that the tether 1124 be moved into the body of the patient (via the skin tissue) along direction X8. The deflection member may be pulled along direction X7 until at least a portion of the tether 1124 passes through the midline incision and is disposed on the internal side of the midline incision. In this embodiment, the tether 1124 (e.g., a portion of the tether 1124 disposed on the external side of the midline incision) may be coupled to the implant 1140 via the L-connector 1142 before or after the deflection member 1110 is moved along direction X7. The deflection member 1110 and the tether 1124 can be pulled through the midline incision and/or the skin tissue (along direction X7) so that the implant 1140 may be placed within the body of the patient.

Figure 12:
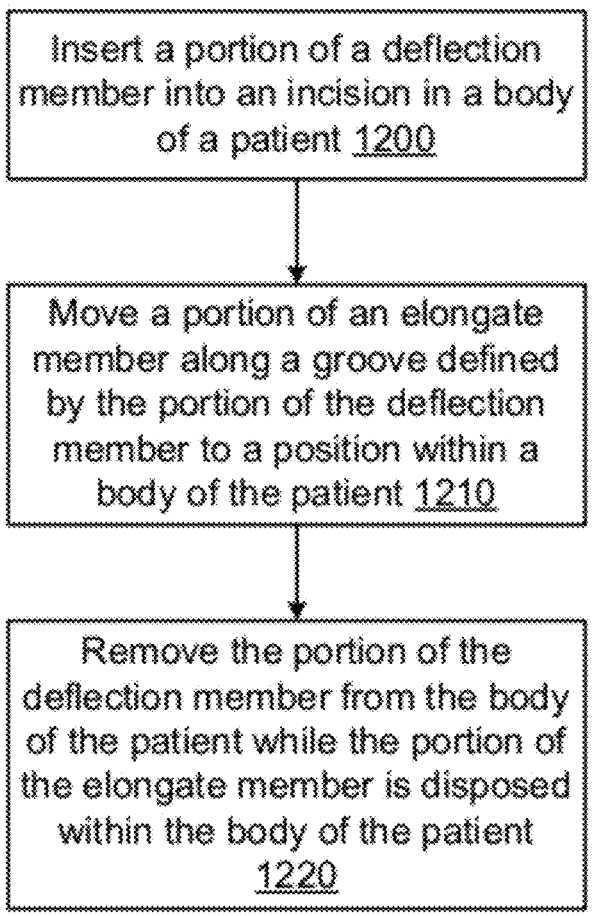
FIG. 12 is a flowchart that illustrates a method for inserting an implant into a body of a patient, according to an embodiment.

FIG. 12 is a flowchart that illustrates a method for inserting an implant into a body of a patient, according to an embodiment. In some embodiments, the implant can be inserted into the body of the patient using a deflection member and an elongate member.

A portion of a deflection member is inserted into an incision in a body of a patient (block 1200). In some embodiments, the deflection member is inserted into the incision using a hemostat coupled to a tab portion of the deflection member.

A portion of an elongate member is moved along a groove defined by the portion of the deflection member to a position within a body of the patient (block 1210). In some embodiments, the groove of the deflection member may extend along the entire length of the deflection member or along only a portion of the length of the deflection member. In some embodiments, the portion of the elongate member may be a piercing portion that can be a wire or a needle.

The deflection member is removed from the body of the patient while the portion of the elongate member is disposed within the body of the patient (block 1220). In some embodiments, the portion of the elongate member disposed within the body of the patient may be a medial portion of a piercing portion the elongate member. In some embodiments, a distal end of the elongate member may be disposed outside of the body of the patient when the deflection member is removed from body of the patient. In some embodiments, an implant may be coupled to a proximal end of the elongate member before the deflection members removed from body of the patient. In some embodiments, after the deflection members removed from the body of the patient, an implant may be coupled to at least a portion (e.g., a proximal portion) of the elongate member. In some embodiments, after an implant has been associated with the elongate member (via a tether portion), at least a portion of the elongate member (e.g., a portion of the piercing portion, a portion of the tether portion) and/or implant may be cut. In some embodiments, the elongate member may have a tether portion to which an implant may be coupled.

In some embodiments, a distal end of the elongate member may be disposed outside of the body of the patient when or before the deflection member is removed from body of the patient. In such embodiments, a lumen of an injection needle may be moved over the distal portion of the elongate member before or after the deflection member is removed from body of the patient. The injection needle may be used to inject a fluid into the body of patient.

In some embodiments, the groove of the deflection member may be facing towards a first side of the body of the patient during the inserting (described at block 1200). The deflection member may be rotated so that the groove faces towards a second side of the body of patient. A first side of an implant may be inserted into the body of the patient while the groove the deflection member is facing towards the first side of the body of the patient. A second side of the implant may be inserted into the body of the patient while the deflection member is facing towards the second side of the body of patient. The first side of the implant and the second side implant may be inserted into the body of the patient using the elongate member, or different elongate members. One or more of the elongate members may be cut during the insertion of the first side of the implant and/or the second side of the implant.

Figure 13A:
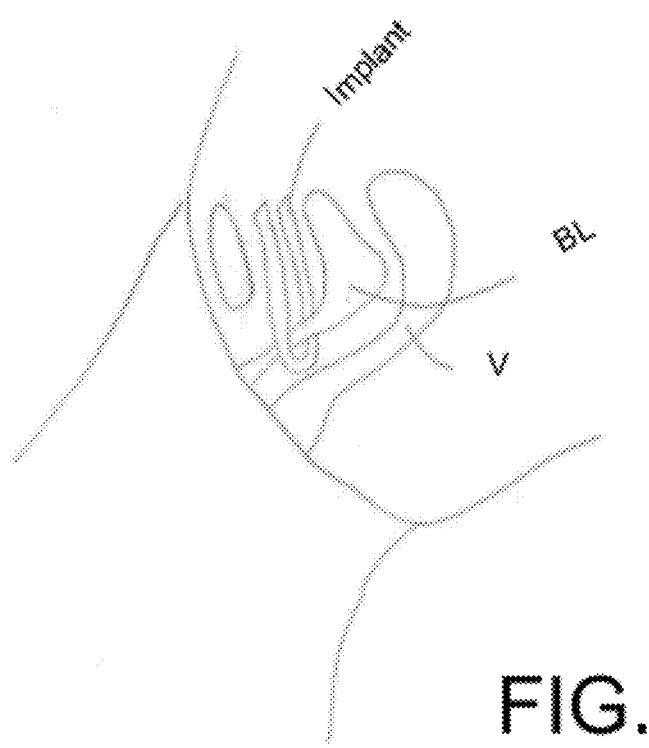
FIGS. 13A through 13D schematically illustrate implants disposed within a body of a patient.

In some embodiments, as schematically illustrated in FIG. 13A, an implant (such as the implant 630 shown in FIG. 6A) can be positioned, at least in part, by the medical devices described herein between a portion of a vagina V of a patient and a portion of a urethra of the patient such that the implant provides support to the urethra of the patient (e.g., via a retropubic approach).

Figure 13B:
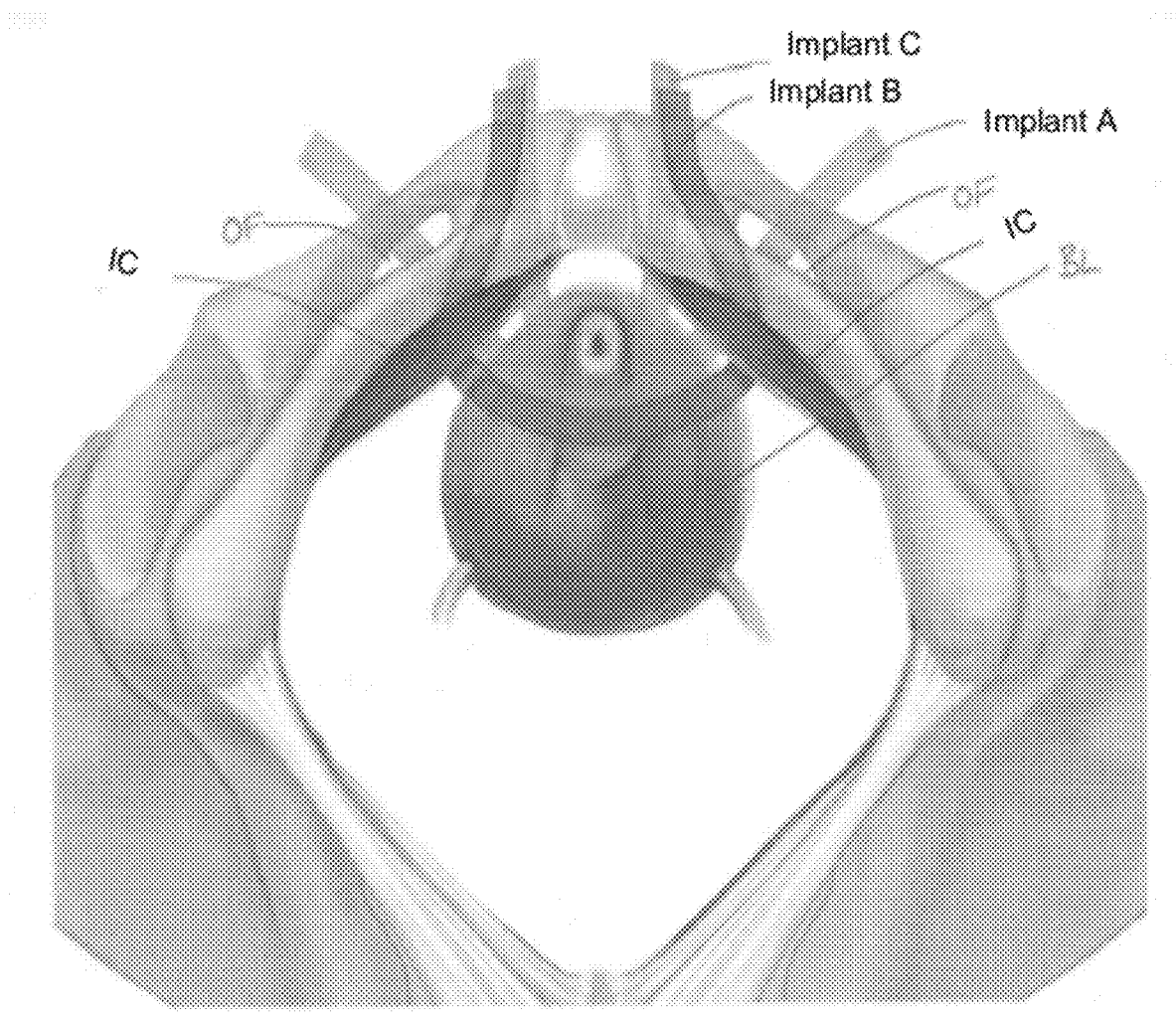
Figure 13C:
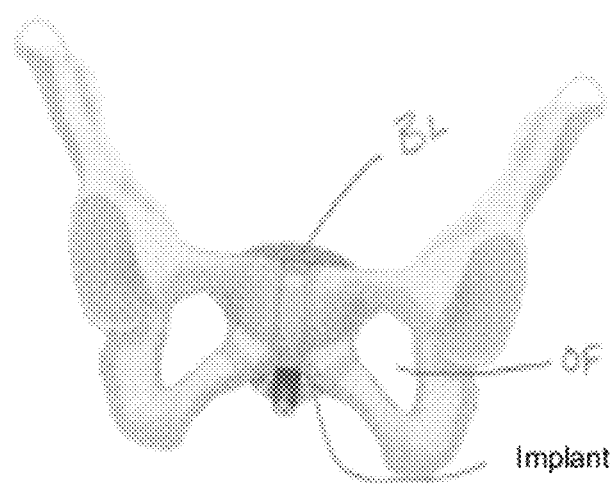
Figure 13D:
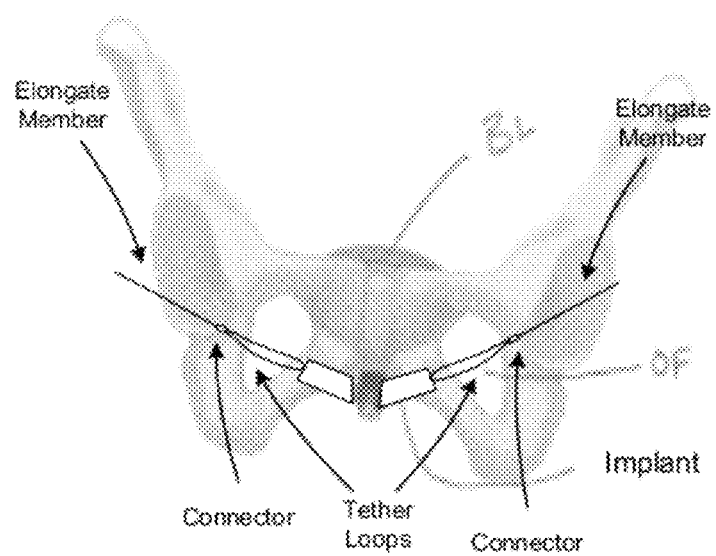

As illustrated in FIG. 13B, an implant (such as the implant 630 shown in FIG. 6A) may be positioned, at least in part, by the medical devices described herein at different locations within the body of the patient. For example, as illustrated in FIG. 13B, implant A may be placed within the body of the patient such that the implant A extends through the obturator foramens OF of the patient. Alternatively, as illustrated, the implant B may extend between the midline incision, Ischiocavernosus muscle IC and in front of the pubic bone (prepubic approach). Alternatively, as illustrated, implant C may be disposed within the body of the patient in a "V" shape (e.g., via a retropubic approach). Although not shown, in some embodiments, the implant B may extend between the ATFP (arcus tendineus facia pelvis) and the obturators of the patient As illustrated in FIG. 13C, an implant (such as the implant 630 shown in FIG. 6A) may be placed, at least in part, by the medical devices described herein such that it extends toward the obturator foramens OF of the patient, but does not extend through the obturator foramens OF. For example, the implant may be disposed within or coupled to muscles disposed proximate the obturator foramens OF. As illustrated in the embodiment shown in FIG. 13D, an implant, tethers, and a connectors remain inside a body of a patient. In some embodiments, at least a portion of the tethers and/or connectors may be disposed outside of the body of the patient (through a skin tissue of the patient) when the implant is disposed within the body of the patient. At least a portion of the elongate members may be disposed outside of the body of the patient (through a skin tissue of the patient). In some embodiments, the medical devices described herein may be used to deliver an implant to the pelvic region of the patient via a retropubic (below) or a suprapubic (above) approach.

FIG. 14 is a diagram that illustrates an implant 1430 (e.g., implant body) disposed within a body of a patient. In this embodiment, a portion 1425 of a tether 1424 (e.g., a tether loop) coupled to an elongate member 1420 via a connector 1420 is disposed within (i.e., internal) the body of the patient and a portion 1423 of the tether 1424 is disposed outside of (i.e., external) the body of the patient. As shown in FIG. 14, the tether 1424 is coupled to the implant 1430. In some embodiments, the tether 1424 can be coupled to the implant 1430 via an L-connector (not shown), hole, suture, and/or other type of connector or mechanism associated with the implant 1430.

In this embodiment, the implant 1430, which is a sling disposed within the body of the patient, can be adjusted (e.g., tensioned) using the tether 1424 and/or the elongate member 1420. After the implant 1430 has been adjusted, a portion of the tether 1424 external to the skin tissue (e.g., portion 1423) can be cut and pulled in direction M to remove the tether 1424 from the implant 1430 and body of the patient. The elongate member 1420 can exit the skin tissue such that it can be pulled to adjust the implant 1430. In some embodiments, the exit site EX at the skin tissue can be approximately 1 mm in diameter. In some embodiments the exit site EX can have a diameter of less than 1 mm (e.g., 0.5 mm) or greater than 1 mm (e.g., 2 mm).

FIG. 15 illustrates a zoomed-in cross-sectional view of a deflection member 1510 that has an X-shaped cross section. As shown in FIG. 15, the deflection member 1510 has a groove 1516 that is open so that at least a portion of an elongate member 1520 is exposed to an ambient environment around the deflection member 1510. The groove 1516 of the deflection member 1510 is configured so that the elongate member 120 may slidably move within the groove 1516 of the deflection member 1510.

Figure 16:
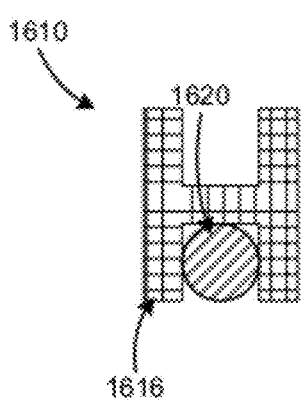
FIG. 16 illustrates a zoomed-in cross-sectional view of a deflection member that has an H-shaped cross section.

FIG. 16 illustrates a zoomed-in cross-sectional view of a deflection member 1610 that has an H-shaped cross section. As shown in FIG. 16, the deflection member 1610 has a groove 1616 that is open so that at least a portion of an elongate member 1620 is exposed to an ambient environment around the deflection member 1610. The groove 1616 of the deflection member 1610 is configured so that the elongate member 120 may slidably move within the groove 1616 of the deflection member 1610.

In one general aspect, a medical device can include an elongate member configured to be associated with an implant and having a piercing portion, and a deflection member having a fixed curvature disposed within a plane. The deflection member can have a distal end configured to be disposed within a body of a patient. The deflection member can define a groove extending along at least a portion of the deflection member. The groove of the deflection member can be configured to deflect the piercing portion of the elongate member.

In some embodiments, the plane is a first plane, and the deflection member can have a tab portion disposed within a second plane non-parallel to the first plane and configured to be received by a grasping device. In some embodiments, the groove is configured to deflect a medial portion of the piercing portion into a position within a pelvic region of the patient when the medial portion of the piercing portion is slidably moved within the groove, and the distal end of the deflection member is configured to be removed from pelvic region of the patient while the medial portion of the piercing portion of the elongate member is within the pelvic region of the patient.

In some embodiments, the apparatus can include a tether portion configured to be coupled to a proximal end of the piercing portion of the elongate member and to the implant. In some embodiments, the fixed curvature has a first portion with a first radius of curvature and a second portion with a second radius of curvature different from the first radius of curvature.

In some embodiments, the groove is defined such that the piercing portion of the elongate member is exposed to a centroid of the fixed curvature of the groove when the elongate member is disposed within the groove. In some embodiments, the deflection member has a clip defining a receiving portion configured to receive a finger of a user. In some embodiments, the groove extends from a proximal end of the deflection member to the distal end of the deflection member.

In another general aspect, a method can include inserting a portion of a deflection member into an incision in a body of a patient, and moving a portion of an elongate member along a groove defined by the portion of the deflection member to a position within a body of the patient. The method can also include removing the portion of the deflection member from the body of the patient while the portion of the elongate member is disposed within the body of the patient.

In some embodiments, the method can also include coupling a hemostat to a tab portion of the deflection member, the moving includes moving the portion of the elongate member along a groove from the tab portion of the elongate member to a distal end of the elongate member. In some embodiments, the groove faces towards a first side of the body of the patient during the inserting, and the method can also include rotating the deflection member such that the groove faces towards a second side of the body of the patient before the removing.

In some embodiments, the method can include associating, after the removing, an implant with the elongate member, and cutting at least a portion of the elongate member after the associating. In some embodiments, the portion of the deflection member is a medial portion of the deflection member. The method can also include moving the medial portion of the elongate member along the groove until a distal portion of the elongate member is disposed outside of the body of the patient, and associating, when the distal portion of the elongate member is disposed outside of the body of the patient, an implant with the elongate member.

In some embodiments, the method can include associating, after the removing, an implant with the portion of the elongate member via a tether portion, and cutting at least a portion of the tether portion after the associating. In some embodiments, the incision is within a vaginal tissue of the patient, and the portion is a distal portion disposed on a first side of the vaginal tissue. The inserting can include inserting the deflection member such that a proximal end of the deflection member is disposed on a second side of the vaginal tissue.

In some embodiments, the method can include moving the elongate member until a distal portion of the elongate member is disposed outside of the body of the patient. The method can also include moving a lumen of an injection needle over the distal portion of the elongate member.

In yet another general aspect, a medical device can include a deflection member defining a groove extending along at least a portion of the deflection member and having a distal portion configured to be inserted into a body of a patient. The deflection member can define a first portion with a first radius of curvature and defining a second portion with a second radius of curvature different from the first radius of curvature. The groove can be configured to receive an elongate member configured to be coupled to an implant and configured to be slidably moved within the groove. The medical device can also include a tab portion coupled to the deflection member.

In some embodiments, the deflection member is disposed within a first plane, and the tab portion is aligned along a second plane non-parallel to the first plane. In some embodiments, the groove is defined such that the elongate member is exposed to a centroid of the first radius of curvature and a centroid of the second radius of curvature when the elongate member is slidably moved within the groove.

In some embodiments, the deflection member defines a helical shape, and the groove has a width substantially equal to a width of the implant. In some embodiments, the groove is configured to deflect a medial portion of the elongate member into a position within a pelvic region of the patient when the medial portion of the elongate member is slidably moved within the groove, and the distal portion of the deflection member is configured to be removed from the pelvic region of the patient while the medial portion of the elongate member is disposed within the pelvic region of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A method for delivering an implant into a pelvic region of a patient, comprising:
    inserting a portion of a deflection member into a body of a patient towards but not through an obturator muscle via a vaginal incision, the deflection member being coupled to a handle portion, the deflection member defining a groove along a surface of the deflection member along at least a portion of a length of the deflection member, the deflection member being curved from a proximal end portion of the deflection member to a distal end portion of the deflection member;
    pushing a needle member such that a distal end portion of the needle member is moved into the groove at the proximal end portion of the deflection member and the distal end portion of the needle member is moved along the groove and then out of the groove and through the obturator muscle until being disposed outside of the body of the patient;
    removing the deflection member from the body of the patient while a portion of the needle member is disposed within the body of the patient; and
    associating the implant with a proximal end portion of the needle member.

2. The method of claim 1, further comprising:
    coupling a hemostat to the handle portion of the deflection member, wherein a curvature of the deflection member is disposed within a plane that is not aligned along a longitudinal axis of the hemostat.

3. The method of claim 1, wherein the groove faces towards a first side of the body of the patient during the inserting,
    the method further comprising:
    rotating the deflection member such that the groove faces towards a second side of the body of the patient before the removing.

4. The method of claim 1, further comprising:
    cutting at least a portion of the needle member after the associating.

5. The method of claim 1, wherein the portion of the needle member is a medial portion of the needle member,
    the method further comprising:
    moving the medial portion of the needle member along the groove until the distal end portion of the needle member is disposed outside of the body of the patient.

6. The method of claim 1, wherein the implant is associated with the proximal end portion of the needle member via a tether portion.

7. The method of claim 1, wherein the incision is within a vaginal tissue of the patient, and the distal end portion of the deflection member is disposed on a first side of the vaginal tissue, the inserting includes inserting the deflection member such that the proximal end portion of the deflection member is disposed on a second side of the vaginal tissue.

8. The method of claim 1, further comprising:
    moving a lumen of an injection needle over the distal end portion of the needle member.

* * * * *